United States Patent
Hoffman et al.

(10) Patent No.: US 11,400,298 B2
(45) Date of Patent: Aug. 2, 2022

(54) POWER SOURCE LONGEVITY

(71) Applicant: Medtronic, Inc., Minneapolis, MN (US)

(72) Inventors: Matthew J. Hoffman, St. Paul, MN (US); Matthew P. Hanly, Scottsdale, AZ (US); Evan S. Johnson, New Brighton, MN (US); Gary J. Pauly, Shoreview, MN (US); Jerry D. Reiland, Coon Rapids, MN (US); Melani G. Sullivan, Minneapolis, MN (US); Ryan D. Wyszynski, Oak Grove, MN (US); Hyun J. Yoon, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 112 days.

(21) Appl. No.: 16/866,178

(22) Filed: May 4, 2020

(65) Prior Publication Data

US 2021/0339028 A1 Nov. 4, 2021

(51) Int. Cl.
*A61N 1/372* (2006.01)
*A61N 1/37* (2006.01)

(52) U.S. Cl.
CPC ....... *A61N 1/3708* (2013.01); *A61N 1/37217* (2013.01)

(58) Field of Classification Search
CPC .. A61N 1/3708; A61N 1/378; A61N 1/37217; A61N 1/37276
See application file for complete search history.

(56) References Cited

U.S. PATENT DOCUMENTS

| | | |
|---|---|---|
| 5,800,472 A | 9/1998 | Mann |
| 6,230,059 B1 | 5/2001 | Duffin |
| 6,412,490 B1 | 7/2002 | Lee |
| 6,668,196 B1 | 12/2003 | Villegas et al. |
| 6,820,019 B1 | 11/2004 | Kelly et al. |
| 8,214,164 B2 | 7/2012 | Gandhi et al. |
| 8,401,646 B2 | 3/2013 | Stadler et al. |
| 8,612,167 B2 | 12/2013 | Schmidt et al. |
| 9,622,778 B2 | 4/2017 | Wengreen et al. |
| 9,750,938 B2 | 9/2017 | Ternes et al. |

(Continued)

OTHER PUBLICATIONS

International Search Report and Written Opinion of International Application No. PCT/US2021/030391, dated Aug. 17, 2021, 8 pp.

*Primary Examiner* — George R Evanisko
(74) *Attorney, Agent, or Firm* — Shumaker & Sieffert, P.A.

(57) ABSTRACT

Techniques are disclosed for using a rate of wireless telemetry of an implantable medical device (IMD) to estimate a remaining longevity of a power source of the IMD. For example, the IMD sets a timer indicative of a remaining power capacity of the power source until a recommended replacement time (RRT) threshold. The IMD determines a power consumption of the IMD due to telemetry and updates, based on the power consumption of the IMD due to telemetry, the timer indicative of the remaining power capacity of the power source. The IMD determines, based on expiration of the timer indicative of the remaining power capacity of the power source, that the power source has reached the RRT threshold. In some examples, the IMD may output, to an external device and for display to a user, an indication that the power source has reached the RRT threshold.

30 Claims, 9 Drawing Sheets

(56) References Cited

U.S. PATENT DOCUMENTS

| | | |
|---|---|---|
| 10,252,062 B2 | 4/2019 | Betzold et al. |
| 10,426,965 B2 | 10/2019 | Bowers |
| 2007/0150018 A1 | 6/2007 | Betzold et al. |
| 2008/0097544 A1 | 4/2008 | Gandhi et al. |
| 2012/0283705 A1 | 11/2012 | Lee et al. |
| 2014/0277248 A1 | 9/2014 | Younker et al. |
| 2015/0157866 A1 | 6/2015 | Demmer et al. |
| 2016/0151631 A1* | 6/2016 | Schilling .............. A61N 1/3756 607/28 |
| 2019/0209847 A1 | 7/2019 | Younker et al. |
| 2021/0001129 A1* | 1/2021 | Pei ........................ A61N 1/378 |

\* cited by examiner

POWER SOURCE LONGEVITY

FIELD

The present technology is generally related to medical systems and, more particularly, implantable medical devices having power sources.

BACKGROUND

Some types of implantable medical devices, such as cardiac pacemakers or implantable cardioverter defibrillators, provide therapeutic electrical stimulation to a heart of a patient via electrodes. The therapeutic electrical stimulation may be delivered to the heart in the form of pulses or shocks for pacing, cardioversion, or defibrillation. In some cases, an implantable medical device may sense intrinsic depolarizations of the heart, and control the delivery of therapeutic stimulation to the heart based on the sensing. Some implantable medical devices provide cardiac sensing functionality without delivery of therapy. Some implantable medical devices are used to provide therapy and/or monitoring for any of a variety of conditions, including neurological or gastrological systems, as examples.

Cardiac resynchronization therapy (CRT) is one type of therapy delivered by an implantable medical device. Cardiac resynchronization therapy may help enhance cardiac output by resynchronizing the electromechanical activity of the ventricles of the heart. Ventricular desynchrony may occur in patients that suffer from congestive heart failure (CHF).

Implantable medical devices are typically powered by internal batteries, and battery depletion is inevitable. Many implantable medical devices are provided with the ability to communicate a "recommended replacement time" (RRT). The RRT informs the clinician that the device's power source is nearing, but has not yet reached end-of-service (EOS), the point at which the power source cannot provide sufficient energy to keep the device operable. The advance warning provided by an RRT gives the clinician the opportunity to take appropriate measures (e.g., to replace the device prior to EOS). Some implantable medical devices derive various estimates of remaining battery life, which may include periodic measurements of battery voltage and either, or both of, battery impedance and current drain. Some implantable medical devices measure and store measurements, including periodic measurements of battery voltage and either, or both of, battery impedance and current drain, that can be communicated to an external instrument to estimate remaining battery life.

SUMMARY

Techniques are disclosed for using a rate of wireless telemetry of an implantable medical device (IMD) to estimate a remaining longevity of a power source of the IMD. For example, the IMD determines that the power source has reached a pre-recommended replacement time (pre-RRT) threshold. In response, the IMD sets a timer indicative of a remaining power capacity of the power source between the pre-RRT threshold and the RRT threshold. The IMD periodically determines a power consumption of the IMD due to wireless telemetry over a previous time interval. The IMD updates the timer based on the power consumption due to telemetry over a time interval. In some examples, the IMD determines an average power consumption over a period of time due to telemetry and uses the average power consumption and the remaining power capacity of the power source indicated by the timer to estimate an amount of time remaining until the IMD reaches the RRT threshold. Furthermore, the IMD may determine that the power source has reached the RRT threshold based on expiration of the timer. The IMD may output, to an external device and for display to a user, an indication of the amount of time remaining until the IMD reaches the RRT threshold or an indication that the power source has reached the RRT threshold.

The techniques of the disclosure may provide specific improvements to the computer-related field of power management for IMDs that have practical applications. For example, the techniques described herein may enable an IMD to more accurately determine when a power source of the IMD may be depleted. By more accurately predicting when the power source of the IMD may be depleted, one may extend the usable capacity of the power source such that an IMD as described herein may remain implanted within the patient for longer periods of time, thereby improving the operational lifespan of the IMD and subjecting the patient to fewer replacement surgeries. Furthermore, the techniques of the disclosure may enable an IMD to more accurately predict when a power source of the IMD may be depleted as a result of historical power usage by the IMD and/or adjust a rate of telemetry by the IMD so as to adjust the rate of power consumption. Such techniques may further increase the longevity of the power source of the IMD and increase the operational lifetime of the IMD.

In one example, this disclosure describes a method comprising: setting, by processing circuitry, a timer indicative of a remaining power capacity of a power source of an implantable medical device (IMD) until a recommended replacement time (RRT) threshold; determining, by the processing circuitry, a power consumption of the IMD due to telemetry; updating, by the processing circuitry and based on the power consumption of the IMD due to telemetry, the timer indicative of the remaining power capacity of the power source; determining, by the processing circuitry and based on expiration of the timer indicative of the remaining power capacity of the power source, that the power source has reached the RRT threshold; and outputting, by the processing circuitry, an indication that the power source has reached the RRT threshold.

In another example, this disclosure describes a system comprising: an implantable medical device (IMD) comprising a power source; and processing circuitry configured to: set a timer indicative of a remaining power capacity of the power source until a recommended replacement time (RRT) threshold; determine a power consumption of the IMD due to telemetry; update, based on the power consumption of the IMD due to telemetry, the timer indicative of the remaining power capacity of the power source; determine, based on expiration of the timer indicative of the remaining power capacity of the power source, that the power source has reached the RRT threshold; and output an indication that the power source has reached the RRT threshold.

In another example, this disclosure describes a non-transitory, computer-readable medium comprising instructions that, when executed, are configured to cause processing circuitry to: set a timer indicative of a remaining power capacity of a power source of an implantable medical device (IMD) until a recommended replacement time (RRT) threshold; determine a power consumption of the IMD due to telemetry; update, based on the power consumption of the IMD due to telemetry, the timer indicative of the remaining power capacity of the power source; determine, based on expiration of the timer indicative of the remaining power capacity of the power source, that the power source has reached the RRT threshold; and output an indication that the power source has reached the RRT threshold.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Like reference characters refer to like elements throughout the figures and description.

DETAILED DESCRIPTION

Figure 1:
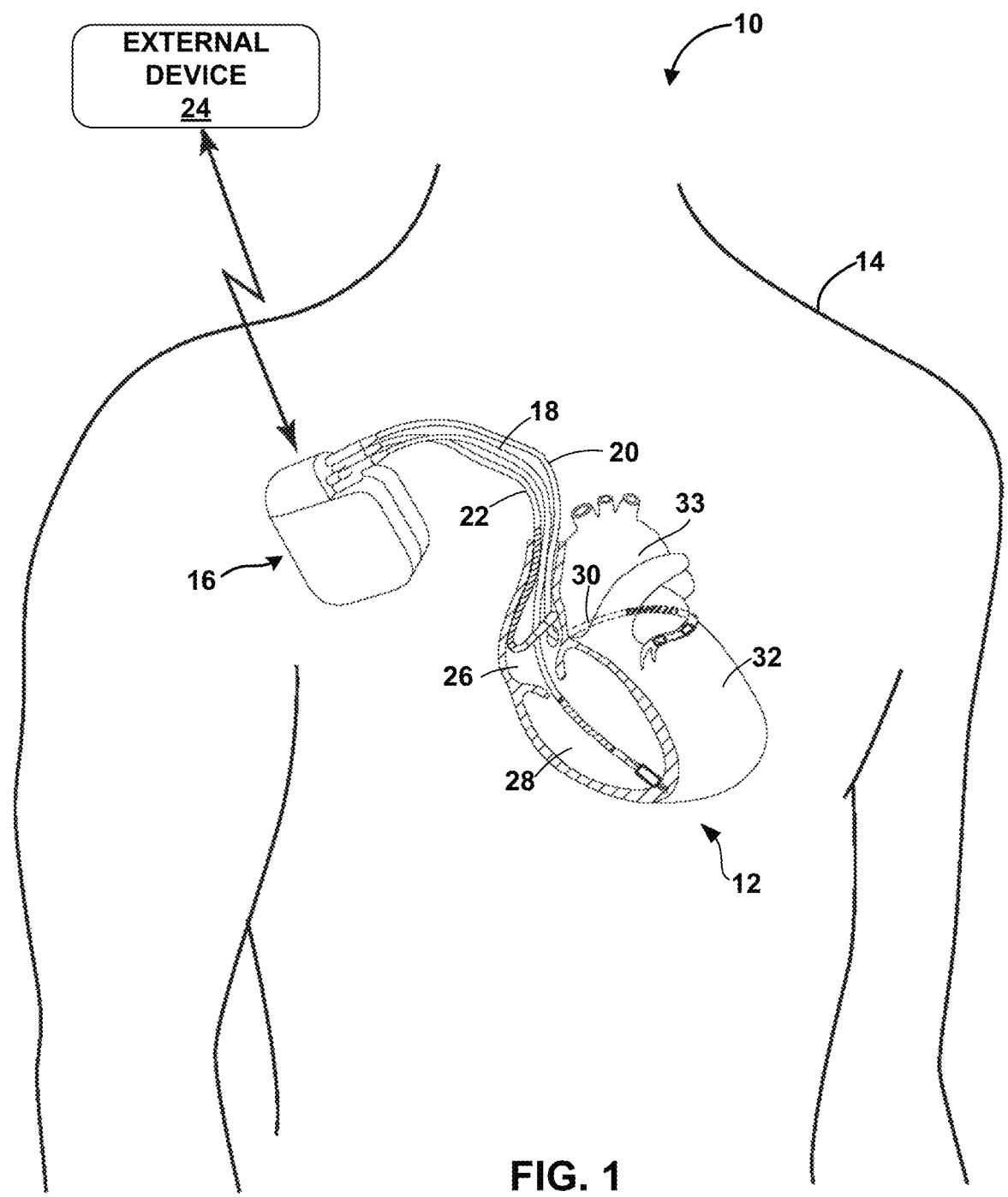
FIG. 1 is conceptual diagram illustrating an example medical device system in conjunction with a patient in accordance with the techniques of the disclosure.

In general, this disclosure is directed to systems and techniques for estimating a remaining longevity of a power source of an IMD. IMDs trade off system performance with power source longevity. For example, the more frequently that the IMD performs high-energy operations, such as wireless telemetry or delivering therapy, the shorter the lifetime of the power source. An IMD typically operates within a patient until sometime after the IMD determines that the power source of the IMD has reached RRT. RRT informs the clinician that the device's power source is nearing, but has not yet reached EOS, the point at which the power source cannot provide sufficient energy to keep the device operable, and therefore replacement of the IMD should be planned. For example, a clinician may set, at a time of implant of the IMD, a simple timer with a value of a parameter estimated to coincide with RRT. The value stored by the timer (e.g., an RRT threshold) may be based on an estimate of power consumption for an average device to reach RRT under normal operating conditions such that the timer expires approximately when the IMD is expected to reach RRT. As another example, the clinician may set an RRT threshold to a value such that when a parameter of the power source of the IMD exceeds the RRT threshold, the IMD indicates RRT. For example, in response to determining that, e.g., a voltage amplitude of the power source is less than the RRT threshold, the IMD may indicate RRT. The clinician may program the RRT threshold to occur earlier than the actual onset of RRT in the power source of the IMD so as to provide sufficient time for the patient to undergo surgery to replace the IMD. This large margin of error accommodates IMDs that consume more power than expected. However, for IMDs capable of efficient, low energy wireless communication (e.g., such as with Bluetooth Low Energy® (BLE)), a rigid timer may lead to significant under-utilization of the available power supplied by the power source. If the RRT could be more accurately predicted, then the IMD may continue to safely operate in the patient for longer periods of time.

The techniques of the disclosure enable an IMD to estimate a remaining longevity of a power source of an IMD based on power consumption due to wireless telemetry. Considering the specific use conditions of the IMD allows more accurate prediction of a remaining life of a power source of an IMD. Exchanging telemetry by the IMD may comprise a majority of the power consumption of the power source of the IMD. Using the techniques described herein, an IMD may adjust a timer indicating a remaining lifetime of the power source when the IMD is operating between the pre-RRT power source service event and the RRT and/or EOS power source service events. For example, an IMD as described herein may implement a capacity-based timer which increments based on device-specific or patient-specific use conditions. Further, an IMD as described herein may implement a capacity-based timer that increments through a known capacity between a value of a trigger parameter threshold (e.g. a pre-RRT threshold voltage) and a value of an end of life parameter threshold (e.g., an RRT or EOS threshold voltage). The power source capacity may be reasonably consistent between different IMDs.

An IMD as described herein incorporates device usage information into an estimate of a remaining longevity of a power source of the IMD. For example, the IMD may incorporate various operations performed by the IMD into the estimate of the remaining power source longevity, such as a rate or frequency of occurrence of wireless communications or advertisements, use conditions of therapy provided to the patient (e.g., a percentage of time where cardiac pacing is delivered, etc.), a rate of sensing operations performed by the IMD, and/or therapy parameter settings that define therapy delivered by the IMD. In some examples, an IMD as described herein implements a timer indicative of an amount of power of the power source remaining until an RRT and/or an EOS service event of the power source. In some examples, the timer may store a value that is approximately equal to a total battery capacity from pre-RRT (e.g., which may occur at a known voltage-based trigger) to RRT or EOS. Further, the IMD adjusts the value stored by the timer to account for variable current drain from the power source occurring as a result of differing usage conditions of the IMD. For example, the IMD may adjust a value stored by the timer based on delivery of therapy by the IMD (e.g., a percentage of time over a time interval where the IMD delivers cardiac pacing), a rate of sensing operations by the IMD, a total amount of telemetry performed by the IMD, a frequency of wireless communications or advertisements transmitted or received by the IMD, etc.) These adjustments to the timer may enable the IMD to accurately estimate a remaining available capacity of the power source, even where the IMD experiences atypical or varying power usage conditions over its lifetime.

Therefore, an IMD as described herein may accurately estimate a time until the RRT is reached based on historical power consumption of the IMD due to telemetry. By accurately predicting the RRT, the IMD may extend the useable lifetime during which the IMD may remain implanted within the patient, thereby subjecting the patient to fewer replacement surgeries.

FIG. 1 illustrates example medical device system 10 in conjunction with patient 14 in accordance with the techniques of the disclosure. Medical device system 10 is an example of a medical device system that is configured to implement the example techniques described herein for determining an estimated remaining longevity of the power source of the IMD (or implantable pulse generator (IPG)), and for indicating service indicators (e.g., power source events), such as pre-RRT and RRT, as described in more detail below.

In some examples, medical device system 10 includes an IMD 16 in communication with external device 24. In the illustrated example, IMD 16 may be coupled to leads 18, 20, and 22. IMD 16 may be, for example, an implantable pacemaker that provides electrical signals to heart 12 and senses electrical activity of heart 12 via electrodes coupled to one or more of leads 18, 20, and 22. IMD 16 may provide cardiac resynchronization therapy (CRT), and may be referred to as a CRT-P device. In the example of FIG. 1, IMD 16 includes cardioversion or defibrillation capabilities.

Although described herein in the context of example IMD 16 that provides electrical therapy to patient 14, the techniques disclosed herein may be used with other types of devices. For example, the techniques may be implemented with one or more of a transcatheter pacemaker configured for implantation within the heart, such as the Micra™ transcatheter pacing system commercially available from Medtronic Inc. of Minneapolis, Minn., an insertable cardiac monitor, such as the Reveal LINQ™ ICM, commercially available from Medtronic Inc. or the LINQ II™ ICM, commercially available from Medtronic Inc., a neurostimulator, a drug delivery device, etc.

Leads 18, 20, 22 extend into heart 12 of patient 14 to sense electrical activity of heart 12 and to deliver electrical stimulation to heart 12. In the example shown in FIG. 1, right ventricular (RV) lead 18 extends through one or more veins (not shown), the superior vena cava (not shown), and right atrium (RA) 26, and into RV 28. Left ventricular (LV) coronary sinus lea 20 extends through one or more veins, the vena cava, right atrium 26, and into the coronary sinus 30 to a region adjacent to the free wall of LV 32 of heart 12. Right atrial (RA) lead 22 extends through one or more veins and the vena cava, and into the RA 26 of heart 12. The example of FIG. 1 depicts IMD 16 as using leads 18, 20, 22. However, in other examples, IMD 16 may be a leadless device that incorporates one or more electrodes into a housing of IMD 16.

IMD 16 may sense electrical signals attendant to the depolarization and repolarization of heart 12 via electrodes (not shown in FIG. 1) coupled to at least one of the leads 18, 20, 22. In some examples, IMD 16 may also sense electrical signals attendant to the depolarization and repolarization of heart 12 via extravascular electrodes (e.g., electrodes positioned outside the vasculature of patient 14), such as epicardial electrodes, external surface electrodes, subcutaneous electrodes, and the like. The configurations of electrodes used by IMD 16 for sensing and pacing may be unipolar or bipolar. In examples where IMD 16 is an implantable cardiac monitoring device, such as an insertable cardiac monitor, IMD 16 may sense patient data, such as electrical activity of heart 12. IMD 16 may store such sensed patient data and upload, on a periodic basis, the sensed patient data to an external device, such as external device 24 or another remote patient monitoring system.

IMD 16 may be configured to provide adaptive CRT to heart 12. In some examples, as part of the adaptive CRT, IMD 16 is configured to deliver at least one of fusion pacing to heart 12 and biventricular pacing to heart 12. In some examples of fusion pacing, IMD 16 may deliver a pacing stimulus (e.g., a pacing pulse) to LV 32 via electrodes of lead 20, where the pacing stimulus is timed such that an evoked depolarization of LV 32 is effected in fusion with the intrinsic depolarization of RV 28, resulting in a ventricular resynchronization. In some examples, when IMD 16 is in a biventricular pacing configuration, IMD 16 may deliver a pacing stimulus (e.g., a pacing pulse) to RV 28 via electrodes of lead 18 and a pacing stimulus to LV 32 via electrodes of lead 20 in a manner that synchronizes activation and contraction of RV 28 and LV 28.

In some examples, the adaptive CRT provided by IMD 16 may be useful for maintaining the cardiac rhythm in patient 14 with a conduction dysfunction, which may result when the natural electrical activation system of heart 12 is disrupted. The natural electrical activation system of a human heart 12 involves several sequential conduction pathways starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and a final distribution to the distal myocardial terminals via the Purkinje fiber network.

CRT delivered by IMD 16 may help alleviate heart failure conditions by restoring synchronous depolarization and contraction of one or more chambers of heart 12. In some cases, the fusion pacing of heart 12 described herein enhances stroke volume of a patient by improving the synchrony with which RV 28 and LV 32 depolarize and contract.

In some examples, external device 24 may be an external programmer, a handheld computing device, or a computer workstation. External device 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. External device 24 can additionally or alternatively include a peripheral pointing device, such as a mouse, via which a user may interact with the user interface. In some embodiments, a display of external device 24 may include a touch screen display, and a user may interact with external device 24 via the display.

A user, such as a physician, technician, or other clinician, may interact with external device 24 to communicate with IMD 16. For example, the user may interact with external device 24 to retrieve physiological or diagnostic information from IMD 16. A user may also interact with external device 24 to program IMD 16, e.g., to select values for operational parameters of the IMD.

For example, the user may use external device 24 to retrieve information from IMD 16 regarding the rhythm of heart 12, trends therein over time, or arrhythmia episodes. As another example, the user may use external device 24 to retrieve information from IMD 16 regarding other sensed physiological parameters of patient 14, such as sensed electrical activity, activity, posture, respiration, or thoracic impedance. As another example, the user may use external device 24 to retrieve information from IMD 16 regarding the performance or integrity of IMD 16 or other components of system 10, such as leads 18, 20, and 22, or a power source of IMD 16. In such examples, physiological parameters of patient 14 and data regarding IMD 16 may be stored in a memory of IMD 16 for retrieval by the user. The user may use external device 24 to program parameters for one or more therapies, such as to select electrodes used to deliver therapies or select waveforms for the therapies, or select or configure one or more detection algorithms for IMD 16 to detect conditions of patient 14.

IMD 16 and external device 24 may communicate via wireless communication using any techniques known in the art. Examples of communication techniques may include, for example, include radiofrequency (RF) telemetry, which may be an RF link established via an antenna according to Bluetooth®, WiFi, or medical implant communication service (MICS), though other techniques are also contemplated. In some examples, external device 24 may include a programming head that may be placed proximate to the patient's body near the IMD 16 implant site in order to improve the quality or security of communication between IMD 16 and external device 24.

In accordance with the techniques of the disclosure, IMD 16 is an example of an IMD that may be configured to determine an estimated remaining longevity of a power source of the IMD. External device 24 is an example of an external device that may include processing circuitry configured to indicate power source events (e.g., a pre-RRT, an RRT, or an EOS for the power source, etc.). The systems and techniques described herein include indicating pre-RRT, RRT, and EOS.

For example, IMD 16 determines that a power source of the IMD has reached a pre-RRT threshold. In response, IMD 16 sets a timer indicative of a remaining power capacity of the power source between the pre-RRT threshold and an RRT threshold. IMD 16 periodically (e.g., once per day, per week, etc.) determines a power consumption of IMD 16 due to telemetry. IMD 16 updates the timer based on the power consumption due to telemetry over a time interval. In some examples, IMD 16 determines an average power consumption over a period of time due to telemetry and uses the average power consumption and the remaining power capacity of the power source indicated by the timer to estimate an amount of time remaining until IMD 16 reaches the RRT threshold. Furthermore, IMD 16 may determine that the power source has reached the RRT threshold based on expiration of the timer. IMD 16 may output, to external device 24, an indication of the amount of time remaining until IMD 16 reaches the RRT threshold or an indication that the power source has reached the RRT threshold. External device 24 displays the indication of the amount of time remaining until the IMD reaches the RRT threshold or the indication that the power source has reached the RRT threshold to a user, such as a clinician.

In the foregoing example, IMD 16 determines a power consumption of IMD 16 due to telemetry. However, in some examples, IMD 16 may determine a power consumption of IMD 16 due to other operations of IMD 16. For example, IMD 16 may determine a power consumption due to one or more parameters defining delivery of therapy by IMD 16 to a patient, a rate or frequency of occurrence of delivery of such therapy, etc. As another example, IMD 16 may determine a power consumption due to one or more parameters defining sensing of a biosignal from the patient, a rate or frequency of occurrence of sensing operations, etc. IMD 16 may use the techniques disclosed herein to determine a power consumption any operation that consumes energy from a power source or that is reflective of any property of the power source of the IMD to estimate an amount of time remaining until IMD 16 reaches the RRT threshold.

The techniques of the disclosure may provide specific improvements to the computer-related field of power management for IMDs that have practical applications. For example, the techniques described herein may enable an IMD, such as IMD 16, to more accurately determine an RRT of a power source of the IMD. By predicting the RRT or other power source condition event with increased accuracy, an IMD as described herein may remain implanted within the patient for longer periods of time, thereby improving the operational lifespan of the IMD and subjecting the patient to fewer replacement surgeries. Furthermore, the techniques of the disclosure may enable an IMD to more accurately estimate the longevity of a power source of the IMD as a result of historical power usage by the IMD and/or adjust a rate of telemetry by the IMD so as to adjust the rate of power consumption. Such techniques may further increase the longevity of the power source of the IMD and increase the operational lifetime of the IMD.

Figure 2:
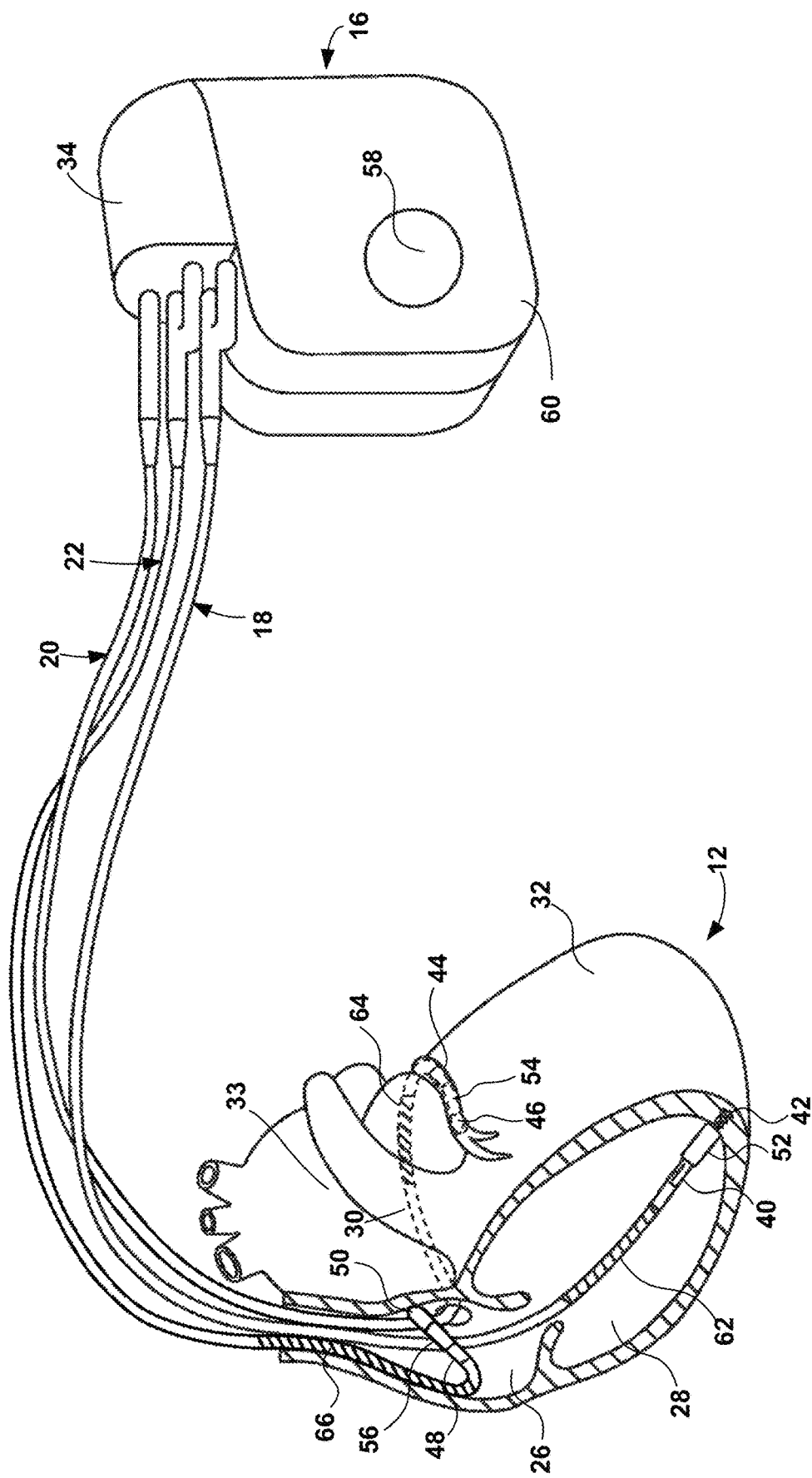
FIG. 2 is a conceptual diagram illustrating the IMD and leads of the medical device system of FIG. 1 in greater detail.

FIG. 2 is a conceptual diagram illustrating IMD 16 and leads 18, 20, 22 of medical device system 10 of FIG. 1 in greater detail. Leads 18, 20, 22 may be electrically coupled to therapy delivery circuitry, sensing circuitry, or other circuitry of IMD 16 via connector block 34. In some examples, proximal ends of leads 18, 20, 22 include electrical contacts that electrically couple to respective electrical contacts within connector block 34. In addition, in some examples, leads 18, 20, 22 are mechanically coupled to connector block 34 with the aid of set screws, connection pins or another suitable mechanical coupling mechanism.

Each of the leads 18, 20, 22 includes an elongated insulative lead body, which may carry a number of conductors separated from one another by tubular insulative sheaths. In the illustrated example, bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. Electrodes 40, 44, and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses to LV 32 via electrodes 44, 46 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48, and 50 may be used for unipolar sensing or stimulation delivery in combination with housing electrode 58. Housing 60 may enclose therapy delivery circuitry that generates cardiac pacing pulses and defibrillation or cardioversion shocks, as well as sensing circuitry for monitoring the patient's heart rhythm.

In some examples, leads 18, 20, 22 may also include elongated electrodes 62, 64, 66, respectively, which may take the form of a coil. IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy, or other materials known to be usable in implantable defibrillation electrodes.

The configuration of medical device system 10 illustrated in FIGS. 1 and 2 is one example, and is not intended to be limiting. In other examples, a monitoring and/or therapy system may include extravascular electrodes, such as subcutaneous electrodes, substernal electrodes, epicardial electrodes, or patch electrodes, instead of or in addition to the electrodes of transvenous leads 18, 20, 22 illustrated in FIG. 1. Further, IMD 16 need not be implanted within patient 14. In examples in which IMD 16 is not implanted in patient 14, IMD 16 may perform cardiac monitoring functions or deliver defibrillation pulses, pacing pulses, and other therapies to heart 12 via percutaneous leads that extend through the skin of patient 14 to a variety of positions within or outside of heart 12.

Figure 3:
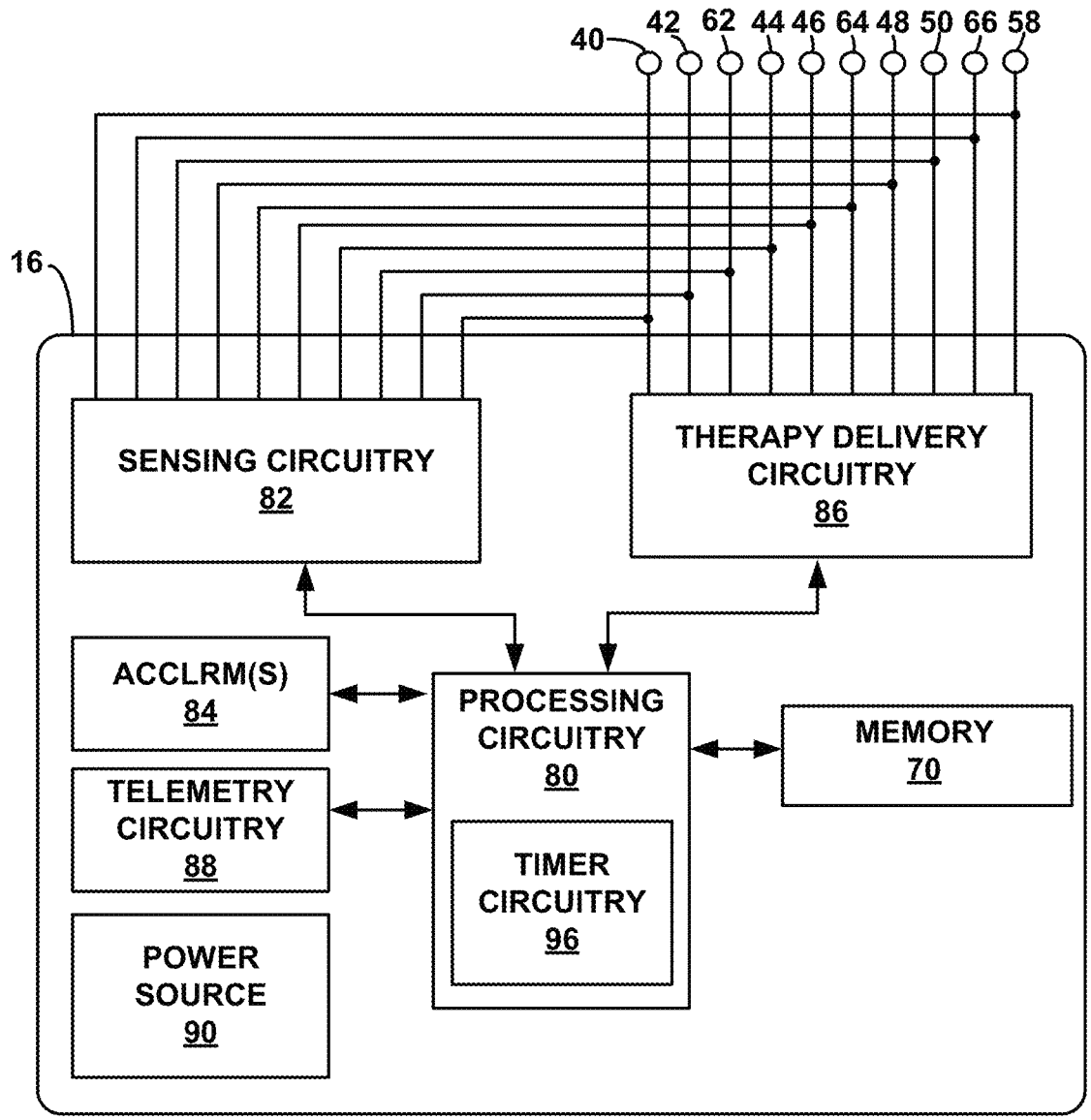
FIG. 3 is a functional block diagram of an example configuration of the IMD of FIG. 1.

In other examples of medical device systems that provide electrical stimulation therapy to heart 12, a therapy system may include any suitable number of leads coupled to IMD 16, and each of the leads may extend to any location within or proximate to heart 12. For example, a therapy system may include a dual chamber device rather than a three-chamber device as shown in FIG. 1. In one example of a dual chamber configuration, IMD 16 is electrically connected to a single lead that includes stimulation and sense electrodes within LV 32 as well as sense and/or stimulation electrodes within RA 26, as shown in FIG. 3. In another example of a dual chamber configuration, IMD 16 is connected to two leads that extend into a respective one of RV 28 and LV 32.

In some examples, a medical device system includes one or more intracardiac pacing devices instead of, or in addition to, an IMD coupled to leads that extend to heart 12, like IMD 16. The intracardiac pacing devices may include therapy delivery and processing circuitry within a housing configured for implantation within one of the chambers of heart 12. In such systems, the plurality of pacing devices, which may include one or more intracardiac pacing devices and/or an IMD coupled to one or more leads, may communicate to coordinate sensing and pacing in various chambers of heart 12 to provide CRT. Processing circuitry and memory of one or more of the pacing devices, and/or another implanted or external medical device, may provide the functionality for controlling delivery of CRT ascribed to processing circuitry and memory of IMD 16 herein.

In some examples, a medical device system includes one or more implantable cardiac monitoring devices instead of, or in addition to, an IMD that delivers electrical stimulation therapy. In such systems, the implantable cardiac monitoring devices may perform cardiac sensing or monitoring functions and upload sensed patient data to an external device, such as external device 24 of FIG. 1.

Further, the techniques for power source monitoring described in this disclosure are not limited to being implemented by devices that deliver CRT or even devices for cardiac therapy and/or monitoring. For example, the techniques of this disclosure may be implemented by neurostimulation devices, or drug pumps. In general, the techniques of this disclosure may be implemented to monitor and indicate the status of a power source of any medical device.

FIG. 3 is a functional block diagram of an example configuration of IMD 16 of FIGS. 1 and 2. In the illustrated example, IMD 16 includes memory 70, processing circuitry 80, sensing circuitry 82, one or more accelerometers 84, therapy delivery circuitry 86, telemetry circuitry 88, and power source 90, one or more of which may be disposed within housing 60 of IMD 16. In some examples, memory 70 includes computer-readable instructions that, when executed by processing circuitry 80, cause IMD 16 and processing circuitry 80 to perform various functions attributed to IMD 16 and processing circuitry 80 herein. Memory 70 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. In addition to sensed physiological parameters of patient 14 (e.g., EGM or ECG signals), one or more time intervals for timing fusion pacing therapy and biventricular pacing therapy to heart 12 may be stored by memory 70.

Processing circuitry 80 may include one or more of a microprocessor, a controller, digital signal processing circuitry (DSP), an application specific integrated circuit (ASIC), a field-programmable gate array (FPGA), or equivalent discrete or integrated logic circuitry. In some examples, processing circuitry 80 may include multiple components, such as any combination of one or more microprocessors, one or more controllers, one or more DSPs, one or more ASICs, or one or more FPGAs, as well as other discrete or integrated logic circuitry. The functions attributed to processing circuitry 80 herein may be embodied as software, firmware, hardware or any combination thereof. Processing circuitry 80 may be configured to determine a heart rate of heart 12 based on electrical activity sensed by sensing circuitry 82.

Processing circuitry 80 may determine one or more operational parameters of IMD 16. For example, power operational modes may be determined (e.g., low, medium, or high power modes). In an example, an IMD operational parameter may include a program, such as type of stimulation being provided (e.g., cardioversion or defibrillation). In an example, such a parameter may include a pulse width, pacing amplitude, pacing rate, pacing percentages, or any combination described herein. These parameters may be used by processing circuitry 80 in calculating the estimated longevity values described herein.

Sensing circuitry 82 is configured to monitor signals from at least one of electrodes 40, 42, 44, 46, 48, 50, 58, 62, 64 or 66 in order to monitor electrical activity of heart 12, such as via EGM signals. For example, sensing circuitry 82 may sense atrial events (e.g., a P-wave) with electrodes 48, 50, 66 within RA 26 or sense an LV 32 event (e.g., an R-wave) with electrodes 44, 46, 64 within LV 32. In some examples, sensing circuitry 82 includes switching circuitry to select which of the available electrodes are used to sense the electrical activity of heart 12. For example, processing circuitry 80 may select the electrodes that function as sense electrodes via the switching circuitry within sensing circuitry 82 (e.g., by providing signals via a data/address bus). In some examples, sensing circuitry 82 includes one or more sensing channels, each of which may comprise an amplifier. In response to the signals from processing circuitry 80, the switching circuitry of sensing circuitry 82 may couple the outputs from the selected electrodes to one of the sensing channels.

In some examples, one channel of sensing circuitry 82 may include an R-wave amplifier that receives signals from electrodes 40 and 42, which are used for pacing and sensing in RV 28 of heart 12. Another channel may include another R-wave amplifier that receives signals from electrodes 44 and 46, which are used for pacing and sensing proximate to LV 32 of heart 12. In some examples, the R-wave amplifiers may take the form of an automatic gain controlled amplifier that provides an adjustable sensing threshold as a function of the measured R-wave amplitude of the heart rhythm. In addition, in some examples, one channel of sensing circuitry 82 may include a P-wave amplifier that receives signals from electrodes 48 and 50, which are used for pacing and sensing in RA 26 of heart 12.

In some examples, sensing circuitry 82 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 70 as an EGM. In some examples, the storage of such EGMs in memory 70 may be under the control of a direct memory access circuit. Processing circuitry 80 may employ digital signal analysis techniques to characterize the digitized signals stored in memory 70 to detect and classify the patient's heart rhythm from the electrical signals. Processing circuitry 80 may detect and classify the heart rhythm of patient 14 by employing any of the numerous signal processing methodologies known in the art.

Signals generated by sensing circuitry 82 may include, for example: an RA-event signal, which indicates a detection of a P-wave via electrodes implanted within RA 26 (FIG. 1); an LA-event signal, which indicates a detection of a P-wave via electrodes implanted within left atrium (LA) 33 (FIG. 1); an RV-event signal, which indicates a detection of an R-wave via electrodes implanted within RV 28; or an LV-event signal, which indicates a detection of an R-wave via electrodes implanted within LV 32. In the example of system 10 shown in FIGS. 1 and 2, IMD 16 is not connected to electrodes that are implanted within LA 33. However, in other example therapy systems, IMD 16 may be connected to electrodes that are implanted within LA 33 in order to sense electrical activity of LA 33.

In some examples, IMD 16 may include one or more additional sensors, such as accelerometers 84. In some examples, accelerometers 84 may comprise one or more three-axis accelerometers. Signals generated by accelerometers 84 may be indicative of, for example, gross body movement of patient 14, such as a patient posture or activity level. Regardless of the configuration of accelerometers 84, processing circuitry 80 may determine patient parameter values based on the signals obtained therefrom. Accelerometers 84 may produce and provide signals to processing circuitry 80 for a determination as to the posture and activity level of patient 14 at a given time. Processing circuitry 80 may then use the determined posture and activity level to further determine whether patient 14 is awake or asleep, and, if patient 14 is determined to be awake, to further determine whether patient 14 is at rest or exercising.

Therapy delivery circuitry 86 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Therapy delivery circuitry 86 is configured to generate and deliver electrical stimulation therapy. For example, therapy delivery circuitry 86 may deliver a pacing stimulus to LV 32 (FIG. 2) of heart 12, in accordance with the fusion pacing techniques described herein, via at least two electrodes 44, 46 (FIG. 2). As another example, therapy delivery circuitry 86 may deliver a pacing stimulus to RV 28 via at least two electrodes 40, 42 (FIG. 2) and a pacing stimulus to LV 32 via at least two electrodes 44, 46 (FIG. 2), e.g., in accordance with the biventricular pacing techniques described herein.

In some examples, therapy delivery circuitry 86 is configured to deliver cardioversion or defibrillation shocks to heart 12. The pacing stimuli, cardioversion shocks, and defibrillation shocks may be in the form of stimulation pulses. In other examples, therapy delivery circuitry 86 may deliver one or more of these types of stimulation in the form of other signals, such as sine waves, square waves, or other substantially continuous time signals.

Therapy delivery circuitry 86 may include a switching circuitry, and processing circuitry 80 may use the switching circuitry to select, e.g., via a data/address bus, which of the available electrodes are used to deliver defibrillation pulses or pacing pulses. The switching circuitry may include a switch array, switch matrix, multiplexer, or any other type of switching device suitable to selectively couple stimulation energy to selected electrodes. In other examples, processing circuitry 80 may select a subset of electrodes 40, 42, 44, 46, 48, 50, 58, 62, 64, and 66 with which stimulation is delivered to heart 12 without a switching circuitry.

Processing circuitry 80 includes timer circuitry 96, which may be embodied as hardware, firmware, software, or any combination thereof. In some examples, processing circuitry 80 is coupled to timer circuitry 96. Timer circuitry 96 may comprise a dedicated hardware circuit, such as an ASIC, separate from other processing circuitry 80 components, such as a microprocessor, or a software module executed by a component of processing circuitry 80 (e.g., a microprocessor or ASIC). Timer circuitry 96 may help control the delivery of pacing pulses to heart 12. Timer circuitry 96 may be configured to determine time stamps of events, determine durations between events, and start and end timers (e.g., countdowns).

In examples in which IMD 16 delivers a pacing pulse according to the one or more A-V interval values selected and/or determined by processing circuitry 80, timer circuitry 96 may include a timer for determining that a selected A-V interval has elapsed after processing circuitry 80 determines that an atrial pace or sense event ($A_{P/S}$, or more generally A) has occurred. The timer circuitry 96 may be configured to begin upon the detection of the preceding atrial pace or sense event ($A_{P/S}$) by processing circuitry 80. Upon expiration of the particular timer, processing circuitry 80 may control therapy delivery circuitry 86 to deliver a pacing stimulus, according to a fusion or biventricular pacing configuration, to heart 12. For example, timer circuitry 96 may generate a trigger signal that triggers the output of a pacing pulse by therapy delivery circuitry 86.

Therapy delivery circuitry 86 may deliver cardioversion or defibrillation shock with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching circuitry of therapy delivery circuitry 86.

Telemetry circuitry 88 includes any suitable hardware, firmware, software or any combination thereof for communicating with another device, such as external device 24 (FIG. 1). Under the control of processing circuitry 80, telemetry circuitry 88 may receive downlink telemetry from and send uplink telemetry to external device 24 with the aid of an antenna, which may be internal and/or external. Processing circuitry 80 may provide the data to be uplinked to external device 24 and the control signals for the telemetry circuit within telemetry circuitry 88, e.g., via an address/data bus. In some examples, telemetry circuitry 88 may provide received data to processing circuitry 80 via a multiplexer.

In some examples, such as where IMD 16 is an implantable cardiac monitoring device, processing circuitry 80 may transmit atrial and ventricular heart signals (e.g., EGM signals) produced by atrial and ventricular sense amp circuits within sensing circuitry 82 to external device 24. Other types of information may also be transmitted to external device 24, such as the various intervals and delays used to deliver CRT. External device 24 may interrogate IMD 16 to receive the heart signals. Processing circuitry 80 may store heart signals within memory 70, and retrieve stored heart signals from memory 70.

Telemetry circuitry 88 includes any suitable hardware, firmware, software or any combination thereof for communicating with another device, such as external device 24 (FIG. 1). Under the control of processing circuitry 80, telemetry circuitry 88 may receive downlink telemetry from and send uplink telemetry to external device 24 with the aid of an antenna, which may be internal and/or external. Processing circuitry 80 may provide the data to be uplinked to external device 24 and the control signals for the telemetry circuit within telemetry circuitry 88 (e.g., via an address/data bus). In some examples, telemetry circuitry 88 may provide received data to processing circuitry 80 via a multiplexer. In some examples, telemetry circuitry 88 of IMD 16 may wirelessly communicate with external programmer 24 of FIG. 1 in accordance with Bluetooth® or BLE®.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis. In some examples, power source 90 may comprise a silver vanadium oxide (SVO) and lithium/carbon monofloride Li/CFx hybrid cathode battery, such as used in IMDs (e.g., pacemakers and defibrillators). In some examples, power source 90 may comprise a generally low impedance battery such as lithium magnesium dioxide (LiMnO2) or lithium silver vanadium oxide (LiSVO). Over the lifetime of power source 90, power source 90 may exhibit a voltage amplitude that comprises a relatively long, flat plateau (e.g., the first plateau as described with respect to FIGS. 6 and 7) followed by a first decline. The first decline in voltage amplitude is followed by a second, shorter plateau that occurs prior to a second decline and onset of EOS of power source 90. By indicating power source events as described herein, the useable life of power source 90 may be extended, for example, by using the relatively large amount of energy in the second plateau that power source 90 is capable of providing prior to onset of EOS.

In some examples, processing circuitry 80 may measure values of one or more parameters of power source 90. For example, processing circuitry 80 may measure a current drain, voltage amplitude such as an instantaneous voltage level or an average voltage level over time, or an impedance of power source 90, etc. In some examples, processing circuitry 80 measures current drain directly. In other examples, processing circuitry 80 estimates a current drain using one or more algorithms. For example, if the current drain of a CPU of processing circuitry 80 per unit of time is known, and an amount of time the CPU of processing circuitry 80 is tasked for a given function is known, processing circuitry 80 may estimate a power capacity used for the amount of time the CPU is tasked for the given function.

In some examples, processing circuitry 80 controls timer circuitry 96 to determine a duration, a time stamp, or control a timer or countdown. An example of a replacement indicator timer for IMDs is described in U.S. Patent Application Publication No. 2007/0150018 by Betzold et al., which is entitled "REPLACEMENT INDICATOR TIMER FOR IMPLANTABLE MEDICAL DEVICES" and is incorporated herein by reference in its entirety.

In some examples, processing circuitry 80 calculates an estimated duration until the power source (e.g., power source 90) reaches a particular service indicator, such as EOS, as described herein. An example of estimating remaining battery service life for IMDs is described in U.S. Pat. No. 8,612,167 to Schmidt et al., which is entitled "ESTIMATING REMAINING BATTERY SERVICE LIFE IN AN IMPLANTABLE MEDICAL DEVICE" and is incorporated herein by reference in its entirety.

In some examples, processing circuitry 80 determines that power source 90 has reached a pre-RRT threshold by measuring one or more parameters of power source 90. In some examples, processing circuitry 80 determines whether a voltage amplitude of power source 90 is less than a value of a first predetermined voltage amplitude (e.g., a pre-RRT voltage amplitude).

In some examples, the first predetermined voltage amplitude is selected from a range of about 1 volt to about 16 volts. In some examples, the first predetermined voltage amplitude is selected from a range of about 1.5 volts to about 2.8 volts. In some examples, the first predetermined voltage amplitude is about 2.625 volts. Other values not expressly described herein may be used for the pre-RRT threshold. As an example, in response to determining that the voltage amplitude of power source 90 is less than 2.625 volts, processing circuitry 80 determines that power source 90 has reached the pre-RRT threshold.

In accordance with the techniques of the disclosure, in response to determining that power source 90 has reached the pre-RRT threshold, processing circuitry 80 controls timer circuitry 96 to set a timer indicative of a remaining power capacity of power source 90 between the pre-RRT threshold and an RRT threshold. As described herein, the timer may comprise one or more countdown timers, counters, clocks, or other digital logic circuits. For example, the timer may be configured to count down or count up. Furthermore, the timer may be configured to count to, e.g., zero, one, or another predetermined value.

In the foregoing example, processing circuitry 80 determines that power source 90 has reached the pre-RRT threshold. In other examples, processing circuitry 80 does not determine the pre-RRT threshold, and instead controls timer circuitry 96 to set a timer indicative of a remaining power capacity of power source 90 from some other point (e.g. an activation time of IMD 16 or an implantation time of IMD 16, etc.) and the RRT.

Processing circuitry 80 determines a power consumption of telemetry circuitry 88. Processing circuitry 80 updates the timer of timer circuitry 96 based on the power consumption due to telemetry. For example, processing circuitry 80 may determine that a remaining capacity of power source 90 is equal to a remaining capacity of power source 90 computed yesterday minus a power capacity determined to have been used by telemetry circuitry 88 today. Processing circuitry 80 may determine the power capacity used by telemetry circuitry 88 during the current time interval to be a function of historical device usage, such as programmed settings, a wireless communication advertisement rate, etc.

For example, on a periodic basis (e.g., once per day, per week, etc.), processing circuitry 80 determines an amount of power consumed by telemetry circuitry 88 over a previous time interval (e.g., a previous day, week, etc.). Processing circuitry 80 decrements the timer by the amount of power consumed by telemetry circuitry 88 over the previous time interval. In some examples, processing circuitry 80 subtracts the amount of power consumed by telemetry circuitry 88 over the previous time interval from the timer. The updated value of the timer is indicative of the remaining power capacity of power source 90 between the pre-RRT threshold and the RRT threshold. In some examples, processing circuitry 80 outputs, to external device 24 via telemetry circuitry 88, an indication of the updated value of the timer indicative of the remaining power capacity of power source 90 until the RRT threshold.

Upon determining that the timer expires, processing circuitry 80 determines that power source 90 has reached the RRT threshold. In some examples, processing circuitry 80 outputs, to external device 24 via telemetry circuitry 88, an indication that power source 90 has reached the RRT threshold. In some examples, processing circuitry 80 may determine that the timer expires upon a value of the timer reaching zero (e.g., such as where the timer is implemented by a countdown timer). In other examples, processing circuitry 80 may determine that the timer expires upon a value of the timer reaching a predetermined value (e.g., such as where the timer is implemented by a counter).

In some examples, IMD 16 may perform telemetry at different rates. For example, IMD 16 may exchange telemetry with external device 24 at a first rate (e.g., a "high" rate) or at a second rate (e.g., a "low" rate) different than the first rate. For example, the first rate may be, e.g., once per minute, and the second rate may be, e.g., once every three minutes. Processing circuitry 80 may store, in memory 70, a value of a first power consumption for the first rate of telemetry and a value of a second power consumption for the second rate of telemetry. As an example, processing circuitry 80 may determine whether, for the previous time interval, IMD 16 telemetered at the first rate or the second rate. Processing circuitry 80 updates the timer of timer circuitry 96 by subtracting the corresponding power consumption values stored in memory 70 from the timer.

As another example, processing circuitry 80 obtains an average power consumption for the previous interval by calculating a fraction of the previous interval during which the IMD 16 telemetered at the first rate and a fraction of the previous interval during which the IMD 16 telemetered at the second rate. Processing circuitry 80 may update the timer of timer circuitry 96 by subtracting the average power consumption for the previous time interval from the timer.

In some examples, memory 70 may store a power consumption value for each telemetric operation performed by IMD 16. Upon performing a telemetric operation, processing circuitry 80 updates the timer of timer circuitry 96 by subtracting the corresponding power consumption value for the telemetric operation from the timer. Telemetric operations performed by IMD 16 and/or telemetry circuitry 88 may include, e.g., broadcasting information to its environment, an advertisement message advertising an availability of IMD 16 to establish a wireless communication session with an external device, a transition of an antenna of telemetry circuitry 88 from a first mode where the antenna is inactive to a second mode where the antenna is active, a wireless connection request transmitted or received by IMD 16, an operation to upload sensed telemetry or patient parametric data to external device 24, an operation to download instructions, such as parameters for performing sensing or therapy delivery by IMD 16, or a communication session established with external device 24. In some examples, processing circuitry 80 counts a number of such telemetric operations performed over the time interval, multiplies the number of such telemetric operations by the power consumption value stored for each telemetric operation, and subtracts the result from the timer of timer circuitry 96 to update the value stored by the timer.

In some examples, processing circuitry 80 additionally may determine that power source 90 has reached the RRT threshold by measuring one or more parameters of power source 90. For example, processing circuitry 80 determines whether a voltage amplitude of power source 90 is less than a value of a second predetermined voltage amplitude (e.g., an RRT voltage amplitude). In some examples, the second predetermined voltage amplitude is selected from a range of about 1 volt to about 16 volts. In some examples, the second predetermined voltage amplitude is selected from a range of about 1.5 volts to about 2.8 volts. In some examples, the second predetermined voltage amplitude is about 2.58 volts. Other values not expressly described herein may be used for the RRT threshold. For example, in response to determining that the voltage amplitude of power source 90 is less than 2.58 volts, processing circuitry 80 determines that power source 90 has reached the pre-RRT threshold. Processing circuitry 80 may use the earlier of the determination that one or more parameters of power source 90 are less than the RRT voltage amplitude or the determination that the timer indicative of the remaining power capacity of power source 90 has expired to determine that power source 90 has reached the pre-RRT threshold.

In some examples, processing circuitry 80 determines an average power consumption over a plurality of time intervals (e.g., such as over a historical lifetime of IMD 16) due to telemetry. Processing circuitry 80 uses the historical average power consumption and the remaining power capacity of power source 90 indicated by the timer of timing circuitry 96 to estimate an amount of time remaining until power source 90 reaches the RRT threshold. For example, processing circuitry 80 may determine that a number of remaining days until power source 90 reaches RRT is equal to a remaining capacity today divided by an average daily current drain, whereupon when the timer expires, processing circuitry 80 determines that RRT (or in some cases, EOS) has occurred.

As an example of the above, processing circuitry 80 may determine that over N days, telemetry circuitry 88 used X milliwatts of power from power source 90. Therefore, for this example, processing circuitry 80 determines that for the lifetime of IMD 16, telemetry circuitry 88 uses $$\frac{X}{N}$$

milliwatts per day. If the timer of timing circuitry 96 indicates that power source 90 has W milliwatts of power remaining until power source 90 reaches the RRT threshold, then processing circuitry 80 may determine that IMD 16 has $$\frac{W}{X/N}$$

days of average operation until power source 90 reaches the RRT threshold. In some examples, processing circuitry 80 outputs, to external device 24 via telemetry circuitry 88, an indication of the amount of time remaining until power source 90 reaches the RRT threshold. In the foregoing example, processing circuitry 80 uses days as a time interval of measurement. However, processing circuitry 80 may use, e.g., seconds, minutes, days, etc. to estimate the amount of time remaining until power source 90 reaches the RRT threshold.

In some examples, processing circuitry 80 may compare the amount of time remaining until power source 90 reaches the RRT threshold to a predetermined threshold. In another example, processing circuitry 80 may compare the remaining power capacity of power source 90 a predetermined threshold. In either event, in response to determining that the predetermined threshold is exceeded, processing circuitry 80 may adjust one or more parameters of IMD 16 so as to conserve power usage and prolong the battery life of power source 90. For example, in response to determining that the remaining power capacity of power source 90 is less than the predetermined threshold, processing circuitry 80 may switch from telemetering at the first rate (e.g., the "high" rate) to telemetering at a second rate (e.g., a "low" rate). In other examples, processing circuitry 80 may adjust one or more parameters that define delivery of therapy to the patient or one or more parameters that define patient parametric data sensing performed by IMD 16.

Figure 4:
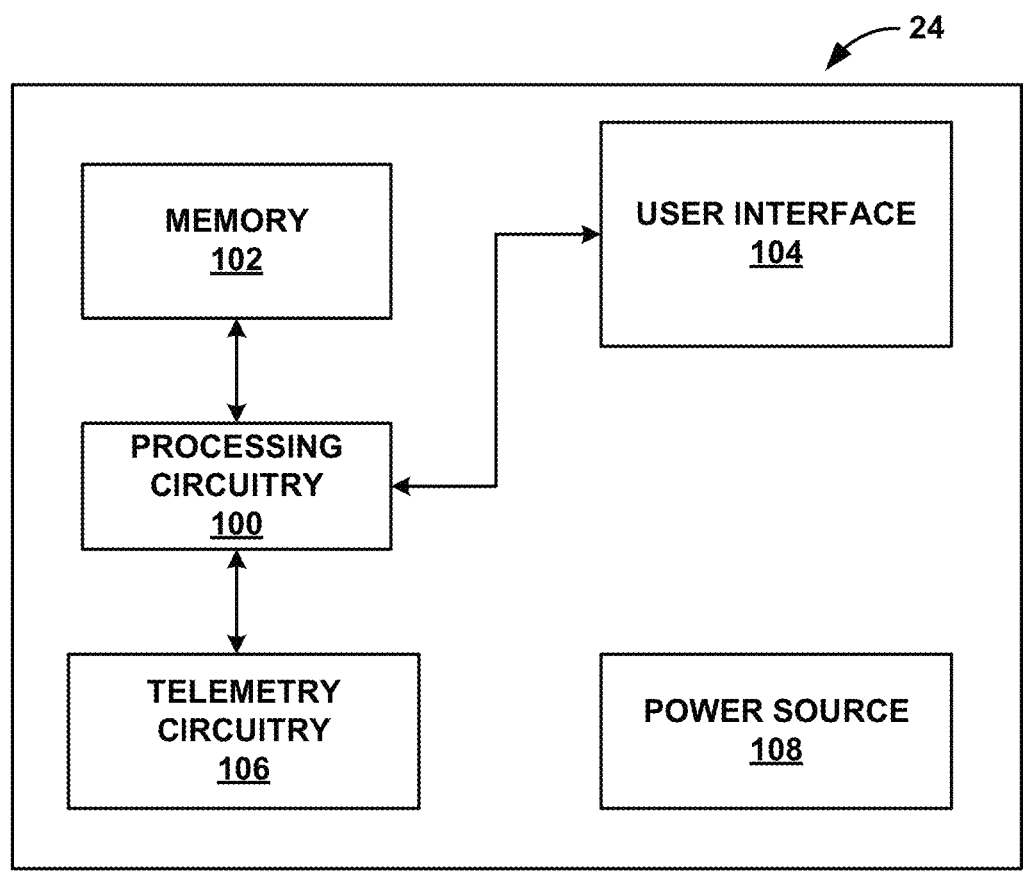
FIG. 4 is a functional block diagram of an example configuration of the external device of FIG. 1.

FIG. 4 is functional block diagram of an example configuration of external device 24 of FIG. 1. As shown in FIG. 4, external device 24 includes processing circuitry 100, a memory 102, a user interface 104, telemetry circuitry 106, and a power source 108. External device 24 may be a dedicated hardware device with dedicated software for interacting with IMD 16. Alternatively, external device 24 may be an off-the-shelf computing device running an application that enables external device 24 to interact with IMD 16.

A user may use external device 24 to select programmable parameters that control the monitoring of patient 14 and delivery of therapy by IMD 16, and to retrieve information collected by IMD 16 regarding the condition of patient 14 or the performance of IMD 16. The user may interact with external device 24 via user interface 104, which may include display to present graphical user interface to a user, and a keypad or another mechanism for receiving input from a user.

Processing circuitry 100 can take the form of one or more microprocessors, DSPs, ASICs, FPGAs, programmable logic circuitry, or the like, and the functions attributed to processing circuitry 100 herein may be embodied as hardware, firmware, software, or any combination thereof. Memory 102 may store instructions that cause processing circuitry 100 to provide the functionality ascribed to external device 24 herein, and information used by processing circuitry 100 to provide the functionality ascribed to external device 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before external device 24 is used to program therapy for another patient. Memory 102 may also store information that controls therapy delivery by IMD 16, such as stimulation parameter values.

External device 24 may communicate wirelessly with IMD 16, such as using RF communication or proximal inductive interaction. This wireless communication is possible through the use of telemetry circuitry 106, which may be coupled to an internal antenna or an external antenna. An external antenna that is coupled to external device 24 may correspond to the programming head that may be placed over heart 12, as described above with reference to FIG. 1.

Telemetry circuitry 106 may be similar to telemetry circuitry 88 of IMD 16 (FIG. 3). Telemetry circuitry 106 may also be configured to communicate with another computing device via wireless communication techniques, or direct communication through a wired connection. Examples of local wireless communication techniques that may be employed to facilitate communication between external device 24 and another computing device include RF communication according to the 802.11, Bluetooth®, or BLE® specification sets, infrared communication, e.g., according to the IrDA standard, or other standard or proprietary telemetry protocols. In this manner, other external devices may be capable of communicating with external device 24 without needing to establish a secure wireless connection. Power source 108 is configured to deliver operating power to the components of external device 24.

In some examples, processing circuitry 100 and memory 102 of external device 24 may be configured to provide some or all of the functionality ascribed to processing circuitry 80 and memory 70 of IMD 16. For example, processing circuitry 100 may be configured with the same or similar functionality as processing circuitry 80, such as for determining an estimated longevity of the power source or indicating power source events. In some examples, processing circuitry 100 may receive data from a memory (e.g., memory 70 of IMD 16 or memory 102 of external device 24), such as via telemetry circuitry 88 of IMD 16 and/or telemetry circuitry 106 of external device 24. In an example, processing circuitry 100 may receive IMD and/or power source information (e.g., voltage signals indicative of the voltage of a power source, such as power source 90 of IMD 16, over time). Processing circuitry 100 may determine whether the voltage signals meet thresholds and/or determine calculations of estimated longevity values of the power, as described further herein. In some examples, processing circuitry 100 may provide an indication (e.g., of a service indicator or an estimated remaining longevity of the power source) to a user, such as via user interface 104.

Processing circuitry 100 may receive, via telemetry circuitry 106, indications of power source service indicators, such as pre-RRT, RRT, EOS, etc. as well as various data related to such power source service indicators. For example, processing circuitry 100 may receive, via telemetry circuitry 106, an indication of a remaining power capacity of power source 90 of IMD 16 between the pre-RRT threshold and the RRT threshold, an indication of the amount of time remaining until power source 90 of IMD 16 reaches the RRT threshold, or an indication that power source 90 has reached the RRT threshold. Processing circuitry 100 outputs, via user interface 104, such indications for display to a user, such as a clinician.

In the example of FIG. 3, processing circuitry 80 of IMD 16 estimated the remaining longevity of power source 90 of IMD 16. However, in other examples, processing circuitry 100 of external device 24 may instead perform the techniques disclosed herein for using a rate of wireless telemetry of IMD 16 to estimate a remaining longevity of power source 90 of IMD 16. In such an example, processing circuitry 100 receives, via telemetry circuitry 106, an indication of one or more values of one or more parameters of power source 90 of IMD 16. For example, processing circuitry 100 receives an indication of a rate of wireless telemetry of IMD 16, a power consumption due to telemetry by IMD 16 over a time period, a remaining capacity of power source 90, etc. Processing circuitry 100 determines, based on the one or more values of the one or more parameters of power source 90 of IMD 16, the power consumption of IMD 16 due to telemetry.

In the example of FIG. 4, external device 24 is described as a single, handheld device that communicates directly with IMD 16 via a wireless communication protocol, such as Bluetooth® or BLE®. However, in other examples, external device 24 may comprise one or more computing devices (e.g., such as a cloud computing system). In such an example, external device 24 may be configured to communicate with IMD 16 via a plurality of computing and networking device via one or more wired and/or wireless networks (e.g., such as the Internet). In some examples, external device 24 may form part of a remote patient monitoring system, such as Carelink® for remotely controlling IMD 16, remotely receiving patient telemetry form IMD 16, or otherwise enabling telemedicine.

Figure 5:
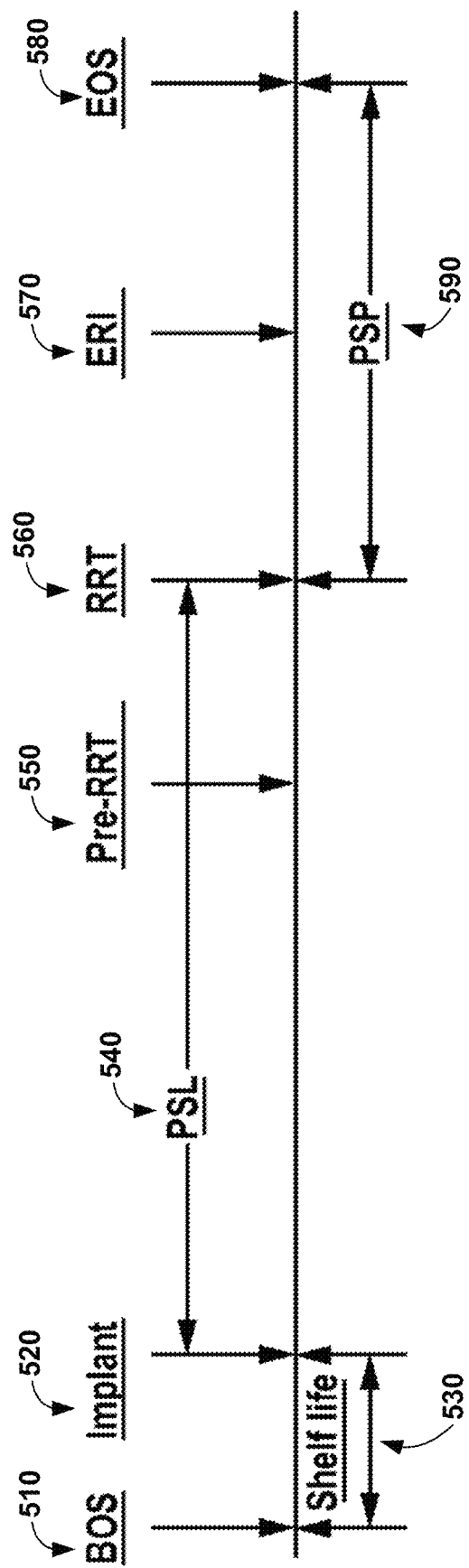
FIG. 5 is a conceptual diagram illustrating relations of events, such as power source service indicators of the IMD of FIG. 1.

FIG. 5 is a conceptual diagram illustrating relations of events, such as power source service indicators, of IMD 16 of FIG. 1. For example, Beginning of Service (BOS) 510 occurs when IMD 16 is first released by the manufacturer as fit for placing on the market. IMD 16 is implanted at Implant 520 mark. Shelf Life 530 is the period between BOS 510 and Implant 520.

Projected Service Life (PSL) 540 is the period from implantation of IMD 16 to Recommended Replacement Time (RRT) 560 under defined conditions. RRT 560 occurs when a power source indicator of IMD 16 reaches a value set by the manufacturer of IMD 16 indicating recommended replacement of IMD 16. In some examples, RRT 560 also indicates entry into Prolonged Service Period (PSP) 590.

Pre-Recommended Replacement Time (pre-RRT) 550 is a threshold that occurs between implant and RRT. Typically, pre-RRT indicates that a power source voltage of IMD 16 is transitioning from a first plateau to a second plateau. Pre-RRT 550 is not a Commission Européenne de Normalisation Électrique (CENELEC) definition. For example, system 10 uses pre-RRT 550 internally and does not necessarily indicate pre-RRT 550 to a user.

PSP 590 is a period beyond RRT 560 during which IMD 16 continues to function as defined by the manufacturer to prolong basic bradyarrhythmia pacing. Elective Replacement Indicator (ERI) 570 is a secondary indicator which is intended to inform a user that IMD 16 has less than 90 days of service remaining. ERI 570 is not a CENELEC definition. End of Service (EOS) 580 occurs when the PSP 590 has elapsed and performance to design specifications cannot be assured.

Figure 6:
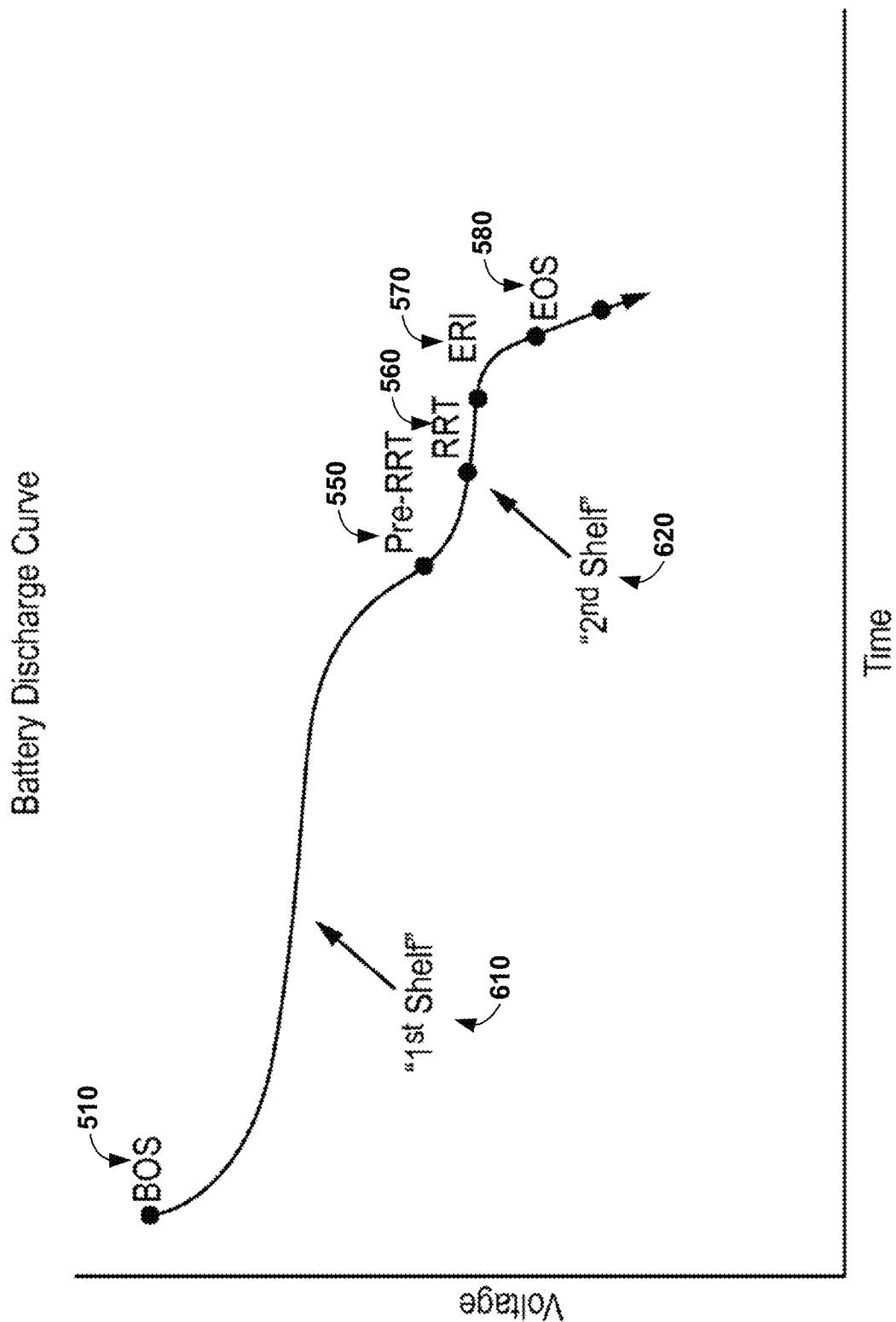
FIG. 6 is a conceptual graph illustrating a power source discharge curve of the IMD of FIG. 1 over time relative to the example power source service indicators of FIG. 5.

FIG. 6 is a conceptual graph illustrating a power source discharge curve of IMD 16 of FIG. 1 over time relative to the example power source service indicators of FIG. 5. For example, first plateau 610 and second plateau 620 are shown relative to example power source indications (e.g., BOS 610, pre-RRT 650, RRT 660, ERI 670, and EOS 680). As illustrated in FIG. 6, first plateau 610 extends for a certain time period until the power source discharge curve quickly decreases, while second plateau 620 extends a shorter time period. After EOS 680, the power source may not have the ability to sufficiently power the circuits of IMD 16.

Figure 7:
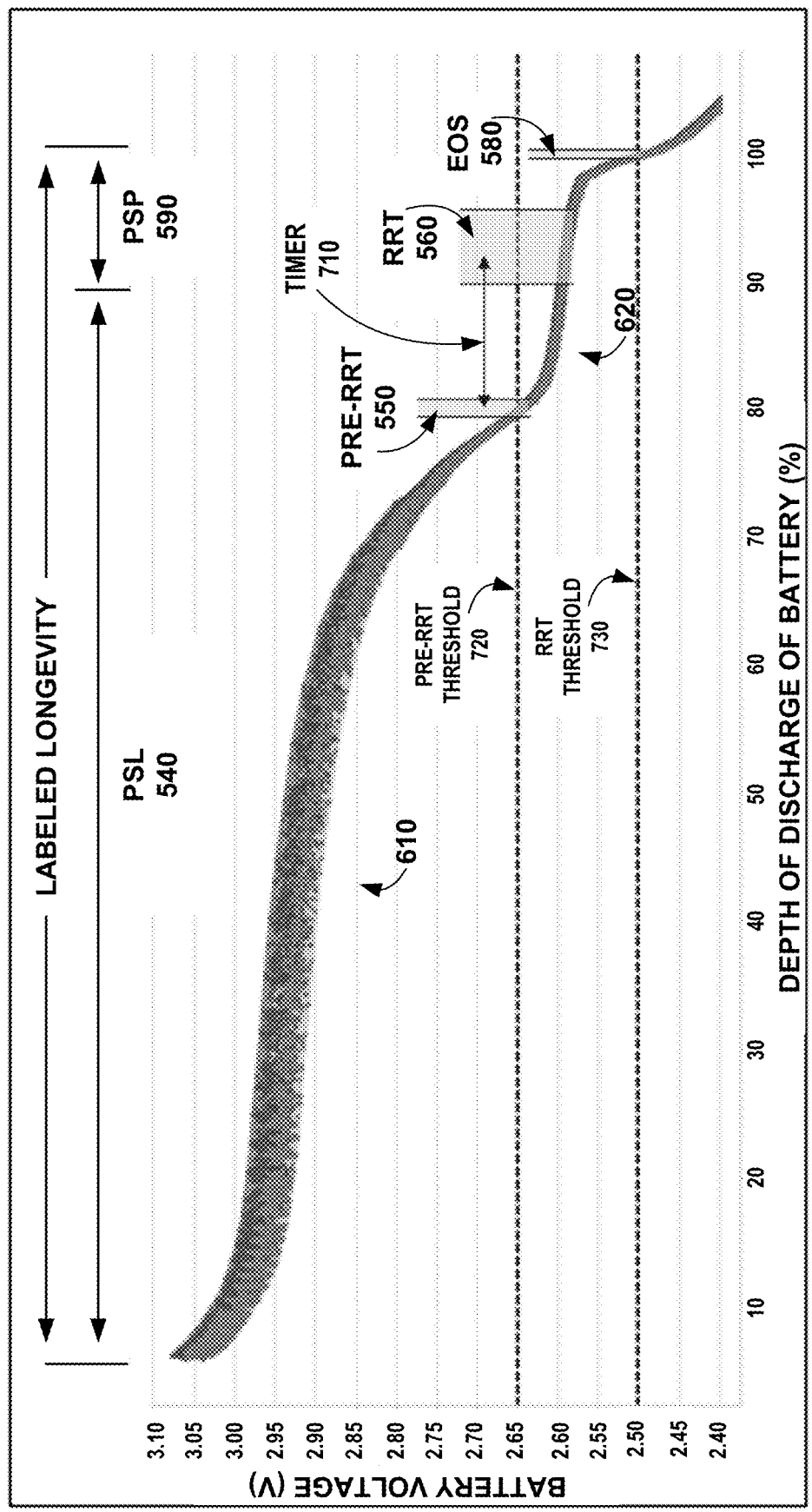
FIG. 7 is a conceptual graph illustrating aspects of the techniques of the disclosure in relation to power source voltage discharge of a battery of an IMD over time and the power source service indicators.

FIG. 7 is a conceptual graph illustrating aspects of the techniques of the disclosure in relation to power source voltage discharge of a battery of an IMD over time and the power source service indicators. FIG. 7 is described with respect to IMD 16 of FIGS. 1 and 3 for convenience. In the example of FIG. 7, the x-axis depicts the depth of discharge of a battery (e.g., power source 90 of IMD 16) from 0 to 100 percent. The y-axis depicts the voltage amplitude of the battery.

In the example of FIG. 7, processing circuitry 80 of IMD 16 determines values of a parameter of power source 90 of IMD 16. The parameter may be a voltage, such as an instantaneous voltage, in some examples. In an example, the parameter is an average voltage, such as measured over a period of days (e.g., 1 to 5 days, such as 3 days). Similarly, the parameter may be a current usage at certain times or over time, a rate of battery depletion, historical depletions (e.g., before recharging the power source), template depletion curves (e.g., the first and second plateau curves as described herein), or another parameter or combination of parameters.

Processing circuitry 80 determines, based on the determined parameter values of the power source, that the parameter reaches pre-RRT voltage threshold 720. Processing circuitry 80 may, but as indicated above does not necessarily, output an indication that pre-RRT 550 has occurred at the time that corresponds to the parameter reaching pre-RRT voltage threshold 720. In the example of FIG. 7, pre-RRT voltage threshold 720 is about 2.65 volts.

In response to determining that the parameter (e.g., voltage) reaches the pre-RRT threshold, processing circuitry 80 may control timer circuitry (e.g., timer circuitry 96, which may be implemented by processing circuitry 80 as described above) to start a pre-RRT to RRT timer 710. In the example of FIG. 7, the pre-RRT to RRT timer 710 is shown as extending from pre-RRT 550 to RRT 560. Processing circuitry 80 determines a power consumption of telemetry circuitry 88. Processing circuitry 80 updates timer 710 based on the power consumption due to telemetry. For example, on a periodic basis (e.g., once per day, per week, etc.), processing circuitry 80 periodically determines an amount of power consumed by telemetry circuitry 88 over a previous time interval (e.g., a previous day, week, etc.). Processing circuitry 80 subtracts the amount of power consumed by telemetry circuitry 88 over the previous time interval from timer 710. The updated value of timer 710 is indicative of the remaining power capacity of power source 90 between pre-RRT 550 and RRT 560. Upon determining that timer 710 has expired (e.g., reached zero or a predetermined threshold), processing circuitry 80 determines that power source 90 has reached RRT 560. In some examples, processing circuitry 80 outputs, to external device 24 via telemetry circuitry 88, an indication that power source 90 has reached RRT 560.

In some examples, RRT voltage threshold 730 may also be set. RRT voltage threshold 730 may be used as an additional mechanism to indicate that power source 90 has reached RRT 560. For example, processing circuitry 80 may determine that power source 90 has reached RRT 560 upon the earlier of pre-RRT to RRT timer 710 expiring or the parameter (e.g., voltage) of power source 90 reaching RRT voltage threshold 730. RRT voltage threshold 730 may be about 2.58 volts. In some examples, RRT voltage threshold 730 is set to be within the second plateau 620.

Figure 8:
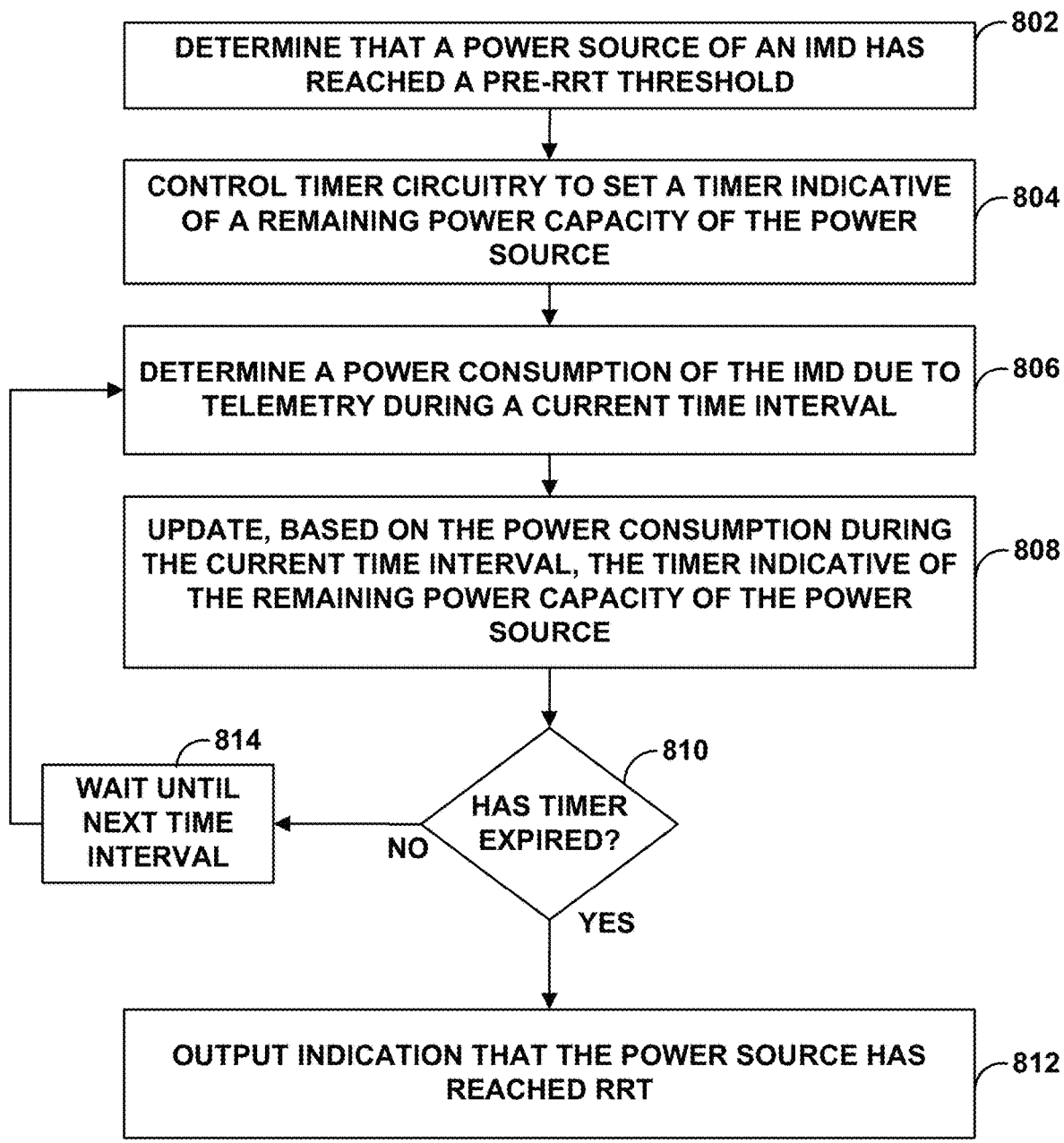
FIG. 8 is a flow chart illustrating an example operation in accordance with the techniques of the disclosure.

FIG. 8 is a flow chart illustrating an example operation in accordance with the techniques of the disclosure. For convenience, FIG. 8 is described with respect to IMD 16 of FIGS. 1 and 3. In some examples, some or all of the operation of FIG. 8 may be performed by one or more other devices, such as processing circuitry 100 of external device 24.

Processing circuitry 80 of IMD 16 determines that power source 90 of IMD 16 has reached a pre-RRT threshold (802). In some examples, processing circuitry 80 determines whether a voltage amplitude of power source 90 is less than a value of a first predetermined voltage amplitude (e.g., a pre-RRT voltage amplitude). In some examples, the first predetermined voltage amplitude is about 2.625 volts. In response to determining that power source 90 has reached the pre-RRT threshold, processing circuitry 80 controls timer circuitry 96 to set a timer indicative of a remaining power capacity of power source 90 between the pre-RRT threshold and an RRT (804).

Processing circuitry 80 determines a power consumption of IM 16 due to wireless telemetry by IMD 16 during a current time interval (806). In some examples, IMD 16 exchanges wireless telemetry with external device 24. For example, processing circuitry 80 determines whether, for the current time interval, IMD 16 telemetered at a first rate (e.g., a "high" rate) or at a second rate (e.g., a "low" rate). For example, the first rate may be, e.g., once per minute, and the second rate may be, e.g., once every three minutes. Processing circuitry 80 may store, in memory 70, a value of a first power consumption for the first rate of telemetry and a value of a second power consumption for the second rate of telemetry. Processing circuitry 80 updates, based on the power consumption of IMD 16, the timer indicative of the remaining power capacity of power source 90 (808). For example, processing circuitry 80 subtracts the corresponding power consumption values stored in memory 70 from the timer.

Processing circuitry 80 determines whether the timer indicative of the remaining power capacity of power source 90 has expired (e.g., is less than or equal to zero or greater than or equal to a threshold) (810). In response to determining that the timer indicative of the remaining power capacity of power source 90 has expired (e.g., "YES" block of 810), processing circuitry 80 outputs, to external device 24 and for display to a user, an indication that the power source has reached the RRT threshold (812).

In response to determining that the timer indicative of the remaining power capacity of power source 90 has not expired (e.g., "NO" block of 810), processing circuitry 80 waits until the next time interval (814) and returns to step 806 to determine a power consumption of IMD 16 due to wireless telemetry by IMD 16 during the next time interval. Therefore, processing circuitry 80 may iteratively update the timer to continuously update an estimate of the remaining power capacity of power source 90 as well as determine whether the power source has reached the RRT threshold.

Figure 9:
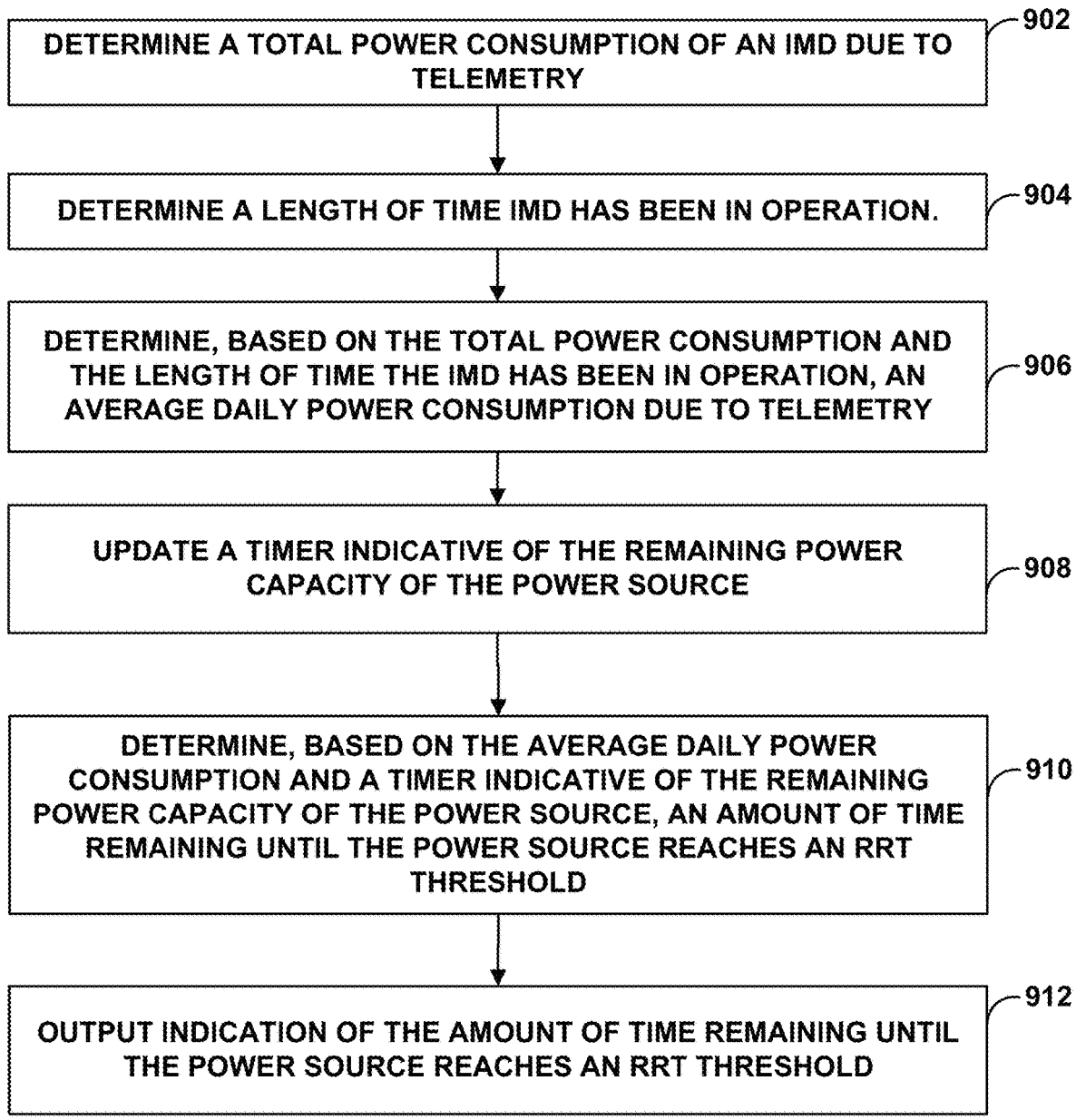
FIG. 9 is a flow chart illustrating another example operation in accordance with the techniques of the disclosure.

FIG. 9 is a flow chart illustrating an example operation in accordance with the techniques of the disclosure. For convenience, FIG. 9 is described with respect to IMP 16 of FIGS. 1 and 3. In some examples, some or all of the operation of FIG. 9 may be performed by one or more other devices, such as processing circuitry 100 of external device 24.

Processing circuitry 80 determines a total power consumption of IMD 16 due to wireless telemetry (902). In some examples, the total power consumption may be a power consumption of IMD 16 due to telemetry from an onset of a pre-RRT threshold to a current time. Further, processing circuitry 80 determines a length of time that IMD 16 has been in operation (904). In some examples, the relevant length of time that IMD 16 has been in operation is the time from the onset of the pre-RRT threshold to the current time.

Processing circuitry 80 determines, based on the length of time that IMD 16 has been in operation and the power consumption of IMD 16 due to wireless telemetry, an average daily power consumption of IMD 16 due to wireless telemetry (906). For example, IMD may divide the power consumption of IMD 16 due to telemetry from the onset of the pre-RRT threshold to the current time by the time from the onset of the pre-RRT threshold to the current time to obtain the daily power consumption of IMD 16 due to telemetry.

Processing circuitry 80 updates a timer indicative of the remaining power capacity of power source 90 (908). In some examples, processing circuitry 80 may update the timer by performing the operation of FIG. 8 described above. Processing circuitry 80 determines, based on the average daily power consumption of IMD 16 due to wireless telemetry and the timer indicative of the remaining power capacity of power source 90, an amount of time remaining until power source 90 reaches the RRT threshold (910). In some examples, the amount of time is a number of minutes, days, weeks, etc. Processing circuitry 80 outputs, to external device 24 and for display to a user, an indication of the amount of time remaining until power source 90 reaches the RRT threshold (912).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Various aspects of the disclosure have been described. These and other aspects are within the scope of the following claims.

What is claimed is:

1. A method comprising:
setting, by processing circuitry using an estimate of power consumption for an average implantable medical device (IMD) to reach a recommended replacement time (RRT), a timer indicative of a remaining power capacity of a power source of an IMD until an RRT threshold;
after setting the timer, performing, by telemetry circuitry of the IMD, one or more telemetric operations over a time interval;
determining, by the processing circuitry, a power consumption of the telemetry circuitry of the IMD over the time interval;
updating, by the processing circuitry and based on the power consumption of the telemetry circuitry of the IMD over the time interval, the timer indicative of the remaining power capacity of the power source;
determining, by the processing circuitry and based on expiration of the timer indicative of the remaining power capacity of the power source, that the power source has reached the RRT threshold; and
responsive to the determination that the power source has reached the RRT threshold, controlling, by the processing circuitry, the telemetry circuitry to output an indication that the power source has reached the RRT threshold for receipt by a second device.

2. The method of claim 1, wherein performing the one or more telemetric operations over the time interval, determining the power consumption of the telemetry circuitry of the IMD over the time interval and updating, based on the power consumption of the telemetry circuitry of the IMD over the time interval, the timer indicative of the remaining power capacity of the power source comprises:
during each time interval of a plurality of time intervals:
performing, by the telemetry circuitry, one or more telemetric operations over the time interval;
determining, by the processing circuitry, a power consumption of the telemetry circuitry of the IMD over the time interval; and
updating, based on the power consumption of the telemetry circuitry of the IMD over the time interval, the timer indicative of the remaining power capacity of the power source.

3. The method of claim 2, further comprising:
determining, by the processing circuitry, an average power consumption of the telemetry circuitry of the IMD over the plurality of time intervals;
determining, by the processing circuitry and based on the average power consumption of the telemetry circuitry of the IMD over the plurality of time intervals and the timer indicative of the remaining power capacity of the power source, an amount of time remaining until the power source reaches the RRT threshold; and
controlling, by the processing circuitry, the telemetry circuitry to output an indication of the amount of time remaining until the power source reaches the RRT threshold for receipt by the second device.

4. The method of claim 3, wherein determining the amount of time remaining until the power source reaches the RRT threshold comprises:
determining, from the average power consumption of the telemetry circuitry of the IMD over the plurality of time intervals and a number of the plurality of time intervals, an average power consumption of the telemetry circuitry of the IMD per time interval; and
determining, based on the average power consumption of the telemetry circuitry of the IMD per time interval and the timer indicative of the remaining power capacity of the power source, an estimate of a number of time intervals remaining until the power source reaches the RRT threshold.

5. The method of claim 1, wherein updating, based on the power consumption of the telemetry circuitry of the IMD over the time interval, the timer indicative of the remaining power capacity of the power source comprises subtracting a value of the power consumption of the telemetry circuitry of the IMD over the time interval from a value of the timer indicative of the remaining power capacity of the power source to obtain an updated value of the timer indicative of the remaining power capacity of the power source.

6. The method of claim 1,
wherein the method further comprises determining, by the processing circuitry, that the power source has reached a pre-recommended replacement time (pre-RRT) threshold, and
wherein setting the timer indicative of the remaining power capacity of the power source is in response to determining that the power source has reached the pre-RRT threshold.

7. The method of claim 6, wherein determining that the power source has reached the pre-RRT threshold comprises determining that a value of a voltage amplitude of the power source is less than a value of a predetermined pre-RRT voltage amplitude threshold.

8. The method of claim 7, wherein the value of the predetermined pre-RRT voltage amplitude threshold is about 1.5 volts to about 2.8 volts.

9. The method of claim 7, wherein determining that the power source has reached the RRT threshold comprises determining that the power source has reached the RRT threshold in response to the earlier of:
determining that the timer indicative of the remaining power capacity of the power source has expired; or
determining that the value of the voltage amplitude of the power source is less than a value of a predetermined RRT voltage amplitude threshold, wherein the value of the predetermined RRT voltage amplitude threshold is less than the value of the predetermined pre-RRT voltage amplitude threshold.

10. The method of claim 9, wherein the value of the predetermined pre-RRT voltage amplitude threshold is about 1.5 volts to about 2.8 volts.

11. The method of claim 1,
wherein the telemetry circuitry is configured to exchange telemetry at a first rate and a second rate, wherein the first rate and second rate are different, and
wherein determining the power consumption of the telemetry circuitry of the IMD over the time interval comprises:
determining a first value of the power consumption of the telemetry circuitry of the IMD over the time interval when exchanging telemetry at the first rate;
determining a second value of the power consumption of the telemetry circuitry of the IMD over the time interval when exchanging telemetry at the second rate; and determining an average power consumption of the telemetry circuitry of the IMD over the time interval from the first value and the second value.

12. The method of claim 1, further comprising:
exchanging, by the telemetry circuitry, telemetry at a first rate;
after updating the timer indicative of the remaining power capacity of the power source, determining that the remaining power capacity of the power source is less than a predetermined threshold; and
in response to determining that the remaining power capacity of the power source is less than the predetermined threshold, controlling, by the processing circuitry, the telemetry circuitry to switch from exchanging telemetry at the first rate to exchanging telemetry at a second rate, wherein the first rate and second rate are different.

13. The method of claim 1, wherein determining the power consumption of the telemetry circuitry of the IMD over the time interval comprises determining, over the time interval, one or more of:
a number of transitions of an antenna of the IMD from a first mode where the antenna is inactive to a second mode where the antenna is active;
a number of connection requests transmitted or received by the IMD;
a number of operations to upload sensed telemetry to an external device;
a number of operations to download instructions from the external device; or
a number of communication sessions established with the external device.

14. The method of claim 1, wherein the indication that the power source has reached the RRT threshold is configured to cause the second device to notify a clinician that the power source has reached the RRT threshold.

15. The method of claim 1,
wherein the processing circuitry comprises processing circuitry of an external device, and
wherein the method further comprises receiving, by the processing circuitry and from the IMD, an indication of one or more values of one or more parameters of the power source of the IMD, and
wherein determining the power consumption of the IMD due to telemetry comprises determining, based on the one or more values of the one or more parameters of the power source of the IMD, the power consumption of the IMD due to telemetry.

16. A system comprising:
an implantable medical device (IMD) comprising a power source and telemetry circuitry; and
processing circuitry configured to set, using an estimate of power consumption for an average IMD to reach a recommended replacement time (RRT), a timer indicative of a remaining power capacity of the power source of the IMD until an RRT threshold,
wherein, after setting the timer, the telemetry circuitry is configured to perform one or more telemetric operations over a time interval, and
wherein the processing circuitry is configured to:
determine a power consumption of the telemetry circuitry of the IMD over the time interval;
update, based on the power consumption of the telemetry circuitry of the IMD over the time interval, the timer indicative of the remaining power capacity of the power source;
determine, based on expiration of the timer indicative of the remaining power capacity of the power source, that the power source has reached the RRT threshold; and
responsive to the determination that the power source has reached the RRT threshold, control the telemetry circuitry to output an indication that the power source has reached the RRT threshold for receipt by a second device.

17. The system of claim 16,
wherein to perform the one or more telemetric operations over the time interval, the telemetry circuitry is configured to perform one or more telemetric operations over each time interval of a plurality of time intervals, and
wherein to determine the power consumption of the telemetry circuitry of the IMD over the time interval and update, based on the power consumption of the telemetry circuitry of the IMD over the time interval, the timer indicative of the remaining power capacity of the power source, the processing circuitry is configured to:
during each time interval of the plurality of time intervals:
determine a power consumption of the telemetry circuitry of the IMD over the time interval; and
update, based on the power consumption of the telemetry circuitry of the IMD over the time interval, the timer indicative of the remaining power capacity of the power source.

18. The system of claim 17, wherein the processing circuitry is further configured to:
determine an average power consumption of the telemetry circuitry of the IMD over the plurality of time intervals;
determine, based on the average power consumption of the telemetry circuitry of the IMD over the plurality of time intervals and the timer indicative of the remaining power capacity of the power source, an amount of time remaining until the power source reaches the RRT threshold; and
control the telemetry circuitry to output an indication of the amount of time remaining until the power source reaches the RRT threshold for receipt by the second device.

19. The system of claim 18, wherein to determine the amount of time remaining until the power source reaches the RRT threshold, the processing circuitry is configured to:
determine, from the average power consumption of the telemetry circuitry of the IMD over the plurality of time intervals and a number of the plurality of time intervals, an average power consumption of the telemetry circuitry of the IMD per time interval; and
determine, based on the average power consumption of the telemetry circuitry of the IMD per time interval and the timer indicative of the remaining power capacity of the power source, an estimate of a number of time intervals remaining until the power source reaches the RRT threshold.

20. The system of claim 16, wherein to update, based on the power consumption of the telemetry circuitry of the IMD over the time interval, the timer indicative of the remaining power capacity of the power source, the processing circuitry is configured to subtract a value of the power consumption of the telemetry circuitry of the IMD over the time interval from a value of the timer indicative of the remaining power capacity of the power source to obtain an updated value of the timer indicative of the remaining power capacity of the power source.

21. The system of claim 16,
wherein the processing circuitry is further configured to determine that the power source of the IMD has reached a pre-recommended replacement time (pre-RRT) threshold, and
wherein the processing circuitry is configured to set the timer indicative of the remaining power capacity of the power source in response to determining that the power source has reached the pre-RRT threshold.

22. The system of claim 21, wherein to determine that the power source has reached the pre-RRT threshold, the processing circuitry is configured to determine that a value of a voltage amplitude of the power source is less than a value of a predetermined pre-RRT voltage amplitude threshold.

23. The system of claim 22, wherein to determine that the power source has reached the RRT threshold, the processing circuitry is configured to determine that the power source has reached the RRT threshold in response to the earlier of:
determining that the timer indicative of the remaining power capacity of the power source has expired; or
determining that the value of the voltage amplitude of the power source is less than a value of a predetermined RRT voltage amplitude threshold, wherein the value of the predetermined RRT voltage amplitude threshold is less than the value of the predetermined pre-RRT voltage amplitude threshold.

24. The system of claim 16,
wherein the telemetry circuitry is configured to exchange telemetry at a first rate and a second rate, wherein the first rate and second rate are different, and
wherein to determine the power consumption of the telemetry circuitry of the IMD over the time interval, the processing circuitry is configured to:
determine a first value of the power consumption of the telemetry circuitry of the IMD over the time interval when exchanging telemetry at the first rate;
determine a second value of the power consumption of the telemetry circuitry of the IMD over the time interval when exchanging telemetry at the second rate; and
determine an average power consumption of the telemetry circuitry of the IMD over the time interval from the first value and the second value.

25. The system of claim 16,
wherein the telemetry circuitry is configured to exchange telemetry at a first rate and a second rate, wherein the first rate and second rate are different, and
wherein the processing circuitry is further configured to:
after updating the timer indicative of the remaining power capacity of the power source, determine that the remaining power capacity of the power source is less than a predetermined threshold; and
in response to determining that the remaining power capacity of the power source is less than the predetermined threshold, control the telemetry circuitry to switch from exchanging telemetry at the first rate to exchanging telemetry at a second rate, wherein the first rate and second rate are different.

26. The system of claim 16,
wherein to determine the power consumption of the telemetry circuitry of the IMD over the time interval, the processing circuitry is configured to determine, over the time interval, one or more of:
a number of transitions of an antenna of the IMD from a first mode where the antenna is inactive to a second mode where the antenna is active;
a number of connection requests transmitted or received by the IMD;
a number of operations to upload sensed telemetry to an external device;
a number of operations to download instructions from the external device; or
a number of communication sessions established with the external device.

27. The system of claim 16, wherein the indication that the power source has reached the RRT threshold is configured to cause the second device to notify a clinician that the power source has reached the RRT threshold.

28. The system of claim 16, wherein the IMD comprises the processing circuitry.

29. The system of claim 16, further comprising an external device, wherein the external device comprises the processing circuitry.

30. A non-transitory, computer-readable medium comprising instructions that, when executed, are configured to cause processing circuitry of an implantable medical device (IMD) to:
set, using an estimate of power consumption for an average IMD to reach a recommended replacement time (RRT), a timer indicative of a remaining power capacity of a power source of the IMD until an RRT threshold;
after setting the timer, control telemetry circuitry of the IMD to perform one or more telemetric operations over a time interval;
determine a power consumption of the telemetry circuitry of the IMD over the time interval;
update, based on the power consumption of the telemetry circuitry of the IMD over the time interval, the timer indicative of the remaining power capacity of the power source;
determine, based on expiration of the timer indicative of the remaining power capacity of the power source, that the power source has reached the RRT threshold; and
responsive to the determination that the power source has reached the RRT threshold, control the telemetry circuitry to output an indication that the power source has reached the RRT threshold for receipt by a second device.

* * * * *